US010309976B2

(12) United States Patent
Johno et al.

(10) Patent No.: US 10,309,976 B2
(45) Date of Patent: Jun. 4, 2019

(54) SUBSTRATE FOR SAMPLE ANALYSIS, SAMPLE ANALYSIS DEVICE, SAMPLE ANALYSIS SYSTEM, AND PROGRAM FOR SAMPLE ANALYSIS SYSTEM

(71) Applicant: PHC HOLDINGS CORPORATION, Tokyo (JP)

(72) Inventors: Masahiro Johno, Ehime (JP); Fusatoshi Okamoto, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 337 days.

(21) Appl. No.: 15/322,910

(22) PCT Filed: Jun. 29, 2015

(86) PCT No.: PCT/JP2015/068722
§ 371 (c)(1),
(2) Date: Dec. 29, 2016

(87) PCT Pub. No.: WO2016/002727
PCT Pub. Date: Jan. 7, 2016

(65) Prior Publication Data
US 2017/0131304 A1    May 11, 2017

(30) Foreign Application Priority Data
Jun. 30, 2014    (JP) ................................ 2014-134777

(51) Int. Cl.
*G01N 21/75* (2006.01)
*G01N 35/00* (2006.01)
(Continued)

(52) U.S. Cl.
CPC ..... *G01N 35/00069* (2013.01); *G01N 33/487* (2013.01); *G01N 33/5302* (2013.01);
(Continued)

(58) Field of Classification Search
CPC ......... G01N 35/00069; G01N 33/5302; G01N 33/487; G01N 35/00584; G01N 2035/00495
See application file for complete search history.

(56) References Cited

U.S. PATENT DOCUMENTS

| 4,495,295 A | 1/1985 | Neurath |
| 4,673,653 A | 6/1987 | Guigan |

(Continued)

FOREIGN PATENT DOCUMENTS

| EP | 0326100 A2 | 8/1989 |
| EP | 0724156 A1 | 7/1996 |

(Continued)

OTHER PUBLICATIONS

International Search Report issued in corresponding International Patent Application No. PCT/JP2015/068729, dated Sep. 1, 2015; with English translation.

(Continued)

*Primary Examiner* — Dennis White
(74) *Attorney, Agent, or Firm* — McDermott Will & Emery LLP

(57) ABSTRACT

A substrate for sample analysis has a rotation axis, a first chamber having a first space for retaining a liquid, a second chamber having a second space for retaining the liquid to be discharged from the first chamber, and a first channel having a path connecting the first chamber and the second chamber. The first space includes a first portion and a second portion, and a coupling portion located between the first and second portions. The substrate includes a wall portion partitioning the first and second portions from each other. The second chamber is more distant from the rotation axis than is the first portion. The coupling portion is closer to the rotation axis than is the wall portion. The second portion at least (Continued)

includes a portion which is more distant from the rotation axis than is the first portion.

16 Claims, 13 Drawing Sheets

(51) Int. Cl.
    *G01N 33/487*    (2006.01)
    *G01N 33/53*     (2006.01)

(52) U.S. Cl.
    CPC ............... *G01N 35/00584* (2013.01); *G01N 2035/00495* (2013.01)

(56) References Cited

U.S. PATENT DOCUMENTS

| | | |
|---|---|---|
| 4,745,077 A | 5/1988 | Holian et al. |
| 4,916,081 A | 4/1990 | Kamada et al. |
| 4,918,025 A | 4/1990 | Grenner |
| 4,990,075 A | 2/1991 | Wogoman |
| 5,160,702 A * | 11/1992 | Kopf-Sill .......... B01L 3/502753 422/72 |
| 5,173,262 A | 12/1992 | Burtis et al. |
| 5,466,574 A | 11/1995 | Liberti et al. |
| 5,627,041 A | 5/1997 | Shartle |
| 5,741,714 A | 4/1998 | Liberti |
| 5,912,134 A | 6/1999 | Shartle |
| 6,063,589 A | 5/2000 | Kellogg et al. |
| 6,103,537 A | 8/2000 | Ullman et al. |
| 6,238,538 B1 | 5/2001 | Parce et al. |
| 6,274,384 B1 | 8/2001 | Starzl et al. |
| 6,458,553 B1 | 10/2002 | Colin et al. |
| 6,551,841 B1 | 4/2003 | Wilding et al. |
| 7,476,543 B2 | 1/2009 | Becker et al. |
| 8,058,010 B2 | 11/2011 | Erickson et al. |
| 8,703,070 B1 | 4/2014 | Parng et al. |
| 2002/0019059 A1 | 2/2002 | Chow et al. |
| 2002/0071788 A1 | 6/2002 | Fujii et al. |
| 2002/0119482 A1 | 8/2002 | Nelson et al. |
| 2002/0151078 A1 | 10/2002 | Kellogg et al. |
| 2002/0180975 A1 | 12/2002 | Ogura et al. |
| 2003/0026740 A1 | 2/2003 | Staats |
| 2003/0077204 A1 | 4/2003 | Seki et al. |
| 2003/0138819 A1 | 7/2003 | Gong et al. |
| 2003/0211010 A1 | 11/2003 | Nagaoka et al. |
| 2004/0089616 A1 | 5/2004 | Kellogg et al. |
| 2004/0137607 A1 | 7/2004 | Tanaami et al. |
| 2004/0181343 A1 | 9/2004 | Wigstrom et al. |
| 2005/0079634 A1 | 4/2005 | Wilding et al. |
| 2005/0123447 A1 | 6/2005 | Koike et al. |
| 2005/0178218 A1 | 8/2005 | Montagu |
| 2005/0221281 A1 | 10/2005 | Ho |
| 2005/0287577 A1 | 12/2005 | Yamamichi |
| 2006/0061760 A1 | 3/2006 | Matsumoto et al. |
| 2006/0263242 A1 | 11/2006 | Yang et al. |
| 2006/0292641 A1 | 12/2006 | Nakanishi et al. |
| 2007/0141576 A1 | 6/2007 | Koide |
| 2007/0160979 A1 | 7/2007 | Andersson |
| 2007/0166721 A1 | 7/2007 | Phan et al. |
| 2007/0189927 A1 | 8/2007 | Ballhorn et al. |
| 2007/0218566 A1 | 9/2007 | Barten et al. |
| 2007/0224304 A1 | 9/2007 | Kunimatsu et al. |
| 2007/0243111 A1 | 10/2007 | Momose |
| 2008/0035579 A1 | 2/2008 | Lee et al. |
| 2008/0073546 A1 | 3/2008 | Andersson et al. |
| 2008/0102537 A1 | 5/2008 | Harding et al. |
| 2008/0131978 A1 | 6/2008 | Fujimura et al. |
| 2008/0138831 A1 | 6/2008 | Hataoka |
| 2008/0156079 A1 | 7/2008 | Momose |
| 2008/0219891 A1 | 9/2008 | McDevitt et al. |
| 2008/0240996 A1 | 10/2008 | Harding et al. |
| 2008/0242556 A1 | 10/2008 | Cao et al. |
| 2009/0042317 A1 | 2/2009 | Ikeda |
| 2009/0053108 A1 | 2/2009 | Cho et al. |
| 2009/0111190 A1 | 4/2009 | Andersson et al. |
| 2009/0123337 A1 | 5/2009 | Noda et al. |
| 2009/0126516 A1 | 5/2009 | Yamamoto et al. |
| 2009/0155125 A1 | 6/2009 | Michiue et al. |
| 2009/0169430 A1 | 7/2009 | Yamamoto et al. |
| 2009/0317896 A1 | 12/2009 | Yoo |
| 2010/0071486 A1 | 3/2010 | Kim et al. |
| 2010/0074801 A1 | 3/2010 | Saiki |
| 2010/0078322 A1 | 4/2010 | Yamanishi et al. |
| 2010/0132820 A1 | 6/2010 | Ozaki et al. |
| 2010/0151560 A1 | 6/2010 | Wo et al. |
| 2010/0159600 A1 | 6/2010 | Shin et al. |
| 2010/0184228 A1 | 7/2010 | Saiki |
| 2010/0221741 A1 | 9/2010 | Saiki et al. |
| 2010/0255589 A1 | 10/2010 | Saiki et al. |
| 2010/0262389 A1 | 10/2010 | Nakanishi et al. |
| 2010/0281961 A1 | 11/2010 | Saiki et al. |
| 2010/0290955 A1 | 11/2010 | Cho et al. |
| 2011/0045505 A1 | 2/2011 | Warthoe et al. |
| 2011/0058985 A1 | 3/2011 | Saiki et al. |
| 2011/0117665 A1 | 5/2011 | Saiki et al. |
| 2011/0124128 A1 | 5/2011 | Oosterbroek et al. |
| 2011/0126646 A1 | 6/2011 | Saiki et al. |
| 2011/0250695 A1 | 10/2011 | Sarofim et al. |
| 2012/0024083 A1 | 2/2012 | Wo et al. |
| 2012/0135533 A1 | 5/2012 | Shikida et al. |
| 2012/0244607 A1 | 9/2012 | Iwamoto et al. |
| 2012/0261256 A1 | 10/2012 | Chang et al. |
| 2012/0269701 A1 | 10/2012 | Linder et al. |
| 2012/0275971 A1 | 11/2012 | Momose |
| 2012/0322683 A1 | 12/2012 | Liu et al. |
| 2013/0029361 A1 | 1/2013 | Hamachi et al. |
| 2013/0074962 A1 | 3/2013 | Garcia da Fonseca et al. |
| 2013/0142697 A1 | 6/2013 | Kim et al. |
| 2013/0260481 A1 | 10/2013 | Shimizu et al. |
| 2013/0261010 A1 | 10/2013 | Bailey et al. |
| 2013/0266956 A1 | 10/2013 | Tia et al. |
| 2013/0288351 A1 | 10/2013 | Nitta |
| 2014/0004505 A1 | 1/2014 | Su et al. |
| 2014/0073041 A1 | 3/2014 | Kijima |
| 2014/0234184 A1 | 8/2014 | Oshika et al. |
| 2014/0242721 A1 | 8/2014 | Kellogg et al. |
| 2014/0270459 A1 | 9/2014 | Moll et al. |
| 2014/0273192 A1 | 9/2014 | Sharpe et al. |
| 2015/0087544 A1 | 3/2015 | Putnam et al. |
| 2015/0093771 A1 | 4/2015 | Griss et al. |
| 2015/0098864 A1 | 4/2015 | Yang |
| 2015/0111778 A1 | 4/2015 | McDevitt et al. |
| 2015/0355132 A1 | 12/2015 | Crooks et al. |

FOREIGN PATENT DOCUMENTS

| | | |
|---|---|---|
| EP | 0871539 A1 | 10/1998 |
| EP | 1105457 A1 | 6/2001 |
| EP | 2072134 A2 | 6/2009 |
| EP | 2133150 A1 | 12/2009 |
| EP | 2253958 A1 | 11/2010 |
| EP | 2311565 A1 | 4/2011 |
| EP | 2402460 A1 | 1/2012 |
| EP | 2602025 A1 | 6/2013 |
| JP | S60-159651 A | 8/1985 |
| JP | S61-264263 A | 11/1986 |
| JP | H01-227061 A | 9/1989 |
| JP | 90/015321 A2 | 12/1990 |
| JP | H05-297001 A | 11/1993 |
| JP | H05-322894 A | 12/1993 |
| JP | H07-500910 A | 1/1995 |
| JP | H08-262024 A | 10/1996 |
| JP | H09-218201 A | 8/1997 |
| JP | H09-257796 A | 10/1997 |
| JP | H09-325148 A | 12/1997 |
| JP | H10-300752 A | 11/1998 |
| JP | 2001-502793 A | 2/2001 |
| JP | 2002-236131 A | 8/2002 |
| JP | 2003-043052 A | 2/2003 |
| JP | 2004-163104 A | 6/2004 |
| JP | 2005-010031 A | 1/2005 |
| JP | 2005-345160 A | 12/2005 |
| JP | 2006-010535 A | 1/2006 |

(56) References Cited

FOREIGN PATENT DOCUMENTS

| | | |
|---|---|---|
| JP | 2006-068384 A | 3/2006 |
| JP | 2006-112824 A | 4/2006 |
| JP | 2006-177850 A | 7/2006 |
| JP | 2006-258696 A | 9/2006 |
| JP | 2007-003361 A | 1/2007 |
| JP | 2007-003414 A | 1/2007 |
| JP | 2007-010341 A | 1/2007 |
| JP | 2007-024851 A | 2/2007 |
| JP | 2007-047031 A | 2/2007 |
| JP | 2007-064742 A | 3/2007 |
| JP | 2007-071557 A | 3/2007 |
| JP | 2007-071655 A | 3/2007 |
| JP | 2007-078676 A | 3/2007 |
| JP | 2007-101240 A | 4/2007 |
| JP | 2007-279069 A | 10/2007 |
| JP | 2007-285792 A | 11/2007 |
| JP | 2008-064701 A | 3/2008 |
| JP | 2008-064748 A | 3/2008 |
| JP | 2008-128906 A | 6/2008 |
| JP | 2008-134126 A | 6/2008 |
| JP | 2008-157708 A | 7/2008 |
| JP | 2008-164360 A | 7/2008 |
| JP | 2008-164434 A | 7/2008 |
| JP | 2008-216237 A | 9/2008 |
| JP | 2009-014529 A | 1/2009 |
| JP | 2009-031116 A | 2/2009 |
| JP | 2009-042104 A | 2/2009 |
| JP | 2009-109251 A | 5/2009 |
| JP | 2009-121860 A | 6/2009 |
| JP | 2009-128342 A | 6/2009 |
| JP | 2009-133831 A | 6/2009 |
| JP | 2009-139289 A | 6/2009 |
| JP | 2009-156717 A | 7/2009 |
| JP | 2009-156778 A | 7/2009 |
| JP | 2009-162701 A | 7/2009 |
| JP | 2009-180688 A | 8/2009 |
| JP | 2009-180697 A | 8/2009 |
| JP | 2009-186296 A | 8/2009 |
| JP | 2009-210564 A | 9/2009 |
| JP | 2009-287971 A | 12/2009 |
| JP | 2010-071644 A | 4/2010 |
| JP | 2010-122022 A | 6/2010 |
| JP | 2010-151447 A | 7/2010 |
| JP | 2010-210531 A | 9/2010 |
| JP | 2010-243373 A | 10/2010 |
| JP | 2010-286297 A | 12/2010 |
| JP | 2011-007778 A | 1/2011 |
| JP | 2011-069618 A | 4/2011 |
| JP | 2011-183589 A | 9/2011 |
| JP | 2011-196849 A | 10/2011 |
| JP | 2012-143204 A | 8/2012 |
| JP | 2012-159325 A | 8/2012 |
| JP | 2012-215515 A | 11/2012 |
| JP | 2012-229985 A | 11/2012 |
| JP | 2013-050435 A | 3/2013 |
| JP | 2013-079812 A | 5/2013 |
| JP | 2013-205305 A | 10/2013 |
| JP | 2014-032018 A | 2/2014 |
| JP | 2014-044077 A | 3/2014 |
| JP | 2014-048209 A | 3/2014 |
| JP | 2014-106207 A | 6/2014 |
| JP | 2014-190906 A | 10/2014 |
| JP | 2014-232023 A | 12/2014 |
| JP | 2015-121493 A | 7/2015 |
| JP | 2015-197338 A | 11/2015 |
| JP | 2015-223562 A | 12/2015 |
| WO | 90/013016 A1 | 11/1990 |
| WO | 92/016844 A1 | 10/1992 |
| WO | 93/08893 A1 | 5/1993 |
| WO | 96/026011 A1 | 8/1996 |
| WO | 98/13684 A1 | 4/1998 |
| WO | 1999/064836 A1 | 12/1999 |
| WO | 01/087485 A2 | 11/2001 |
| WO | 02/23163 A1 | 3/2002 |
| WO | 05/075997 A1 | 8/2005 |
| WO | 2007/005077 A1 | 1/2007 |
| WO | 2007/105584 A1 | 9/2007 |
| WO | 2007/116909 A1 | 10/2007 |
| WO | 07/122943 A1 | 11/2007 |
| WO | 2008/053743 A1 | 5/2008 |
| WO | 2008/139697 A1 | 11/2008 |
| WO | 2010/044598 A2 | 4/2010 |
| WO | 10/058303 A1 | 5/2010 |
| WO | 2010/077159 A1 | 7/2010 |
| WO | 2012/164552 A1 | 12/2012 |
| WO | 2014/017018 A1 | 1/2014 |

OTHER PUBLICATIONS

International Search Report issued in corresponding International Patent Application No. PCT/JP2015/068724, dated Sep. 1, 2015; with English translation.
International Search Report issued in corresponding International Patent Application No. PCT/JP2015/068723, dated Sep. 29, 2015; with English translation.
International Search Report issued in corresponding International Patent Application No. PCT/JP2015/068722, dated Sep. 29, 2015; with English translation.
Chinese Search Report issued in Chinese Patent Application No. 201580035558.6, dated Dec. 15, 2017; with partial English translation.
Extended European Search Report dated Dec. 21, 2017, issued in counterpart European Patent Application No. 15814780.1.
Non-Final Office Action issued in related U.S. Appl. No. 15/323,007, dated Jan. 4, 2019.

* cited by examiner

SUBSTRATE FOR SAMPLE ANALYSIS, SAMPLE ANALYSIS DEVICE, SAMPLE ANALYSIS SYSTEM, AND PROGRAM FOR SAMPLE ANALYSIS SYSTEM

RELATED APPLICATIONS

This application is the U.S. National Phase under 35 U.S.C. § 371 of International Application No. PCT/JP2015/068722, filed on Jun. 29, 2015, which in turn claims the benefit of Japanese Application No. 2014-134777, filed on Jun. 30, 2014, the disclosures of which are incorporated by reference herein.

TECHNICAL FIELD

The present application relates to a substrate for sample analysis, a sample analysis device, a sample analysis system, and a program for a sample analysis system.

BACKGROUND ART

Techniques have been known which utilize a substrate for sample analysis in order to analyze a specific component within an analyte, such as urine or blood. For example, Patent Document 1 discloses a technique that utilizes a disk-shaped substrate for sample analysis, on which channels, chambers, and the like are formed. In this technique, the substrate for sample analysis is allowed to rotate, etc., thereby effecting transfer, distribution, mixing of solutions, analysis of components within an analyte solution, and so on.

CITATION LIST

Patent Literature

[Patent Document 1] Japanese National Phase PCT Laid-Open Publication No, 7-500910

SUMMARY OF INVENTION

Technical Problem

Analysis of specific components within an analyte includes assay techniques which utilize enzymatic reaction, immunoreaction, and the like, and involve complicated reaction steps. There has been a desire for a technique which allows assay techniques that involve such complicated reaction steps to be performed in a substrate for sample analysis.

A non-limiting, illustrative embodiment of the present application provides a substrate for sample analysis, a sample analysis device, a sample analysis system, and a program for a sample analysis system which support assay techniques that carry out analysis components within an analyte through more complicated reaction steps.

Solution to Problem

A substrate for sample analysis according to one aspect of the present application is a substrate for sample analysis on which transfer of a liquid is to occur with rotational motion, comprising: a substrate having a rotation axis; a first chamber being located in the substrate and having a first space for retaining a liquid; a second chamber being located in the substrate and having a second space for retaining the liquid to be discharged from the first chamber; and a first channel being located in the substrate and having a path connecting the first chamber and the second chamber, the first channel being capable of being filled via capillary action with the liquid retained in the first space, wherein, the first space of the first chamber includes a first portion and a second portion, and a coupling portion being located between the first portion and the second portion and coupling the first portion and the second portion; the substrate has a wall portion partitioning the first portion and the second portion of the first space from each other; the second chamber is more distant from the rotation axis than is the first portion of the first chamber; the coupling portion of the first space is closer to the rotation axis than is the wall portion of the substrate; and the second portion of the first space at least includes a portion which is more distant from the rotation axis than is the first portion.

Advantageous Effects of Invention

A substrate for sample analysis, a sample analysis device, a sample analysis system, and a program for a sample analysis system according to one aspect of the present application support assay techniques that carry out analysis of components within an analyte through assay techniques that carry out analysis of components within an analyte through complicated reaction steps.

DESCRIPTION OF EMBODIMENTS

Assay techniques for components within an analyte such as urine or blood may utilize a combination reaction between the analyte being the subject fog analysis and a ligand which specifically binds to the analyte. Examples of such assay techniques include immunoassay techniques and genetic diagnosis techniques.

Examples of immunoassay techniques are competitive assays and non-competitive assays (sandwich immunoassay). Examples of genetic diagnosis techniques are genetic detection techniques based on hybridization. In these immunoassay techniques and genetic detection techniques, magnetic particles (which may also be referred to as "magnetic beads", "magnetism particles", "magnetism beads", etc.) are used, for example. As an example of such assay techniques, a sandwich immunoassay utilizing magnetic particles will be specifically described.

Figure 1:
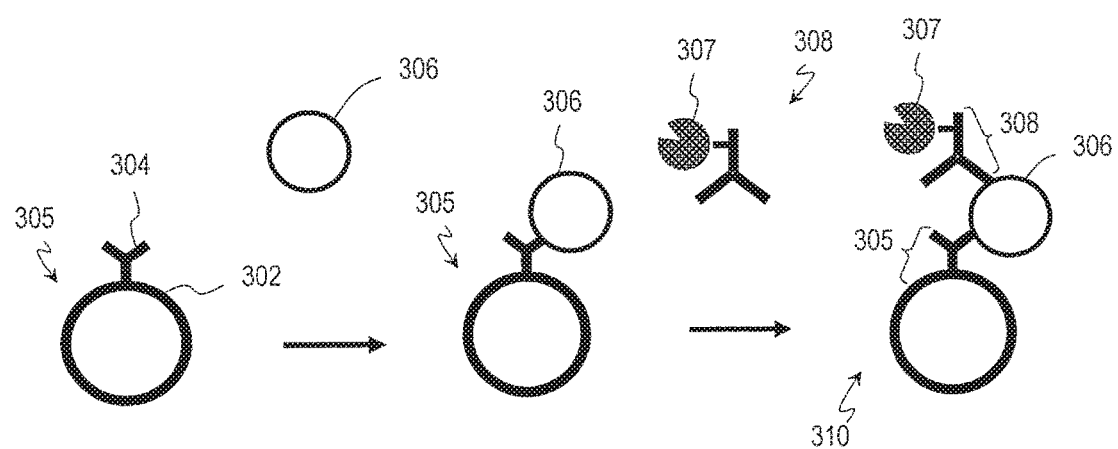
FIG. 1 An exemplary schematic diagram describing a sandwich immunoassay utilizing magnetic particles.

As shown in FIG. 1, first, a primary antibody 304 having a magnetic particle 302 immobilized to whose surface (hereinafter referred to as the "magnetic-particle-immobilized antibody 305") and, an antigen 306, for which measurements are to be taken, are allowed bind through an antigen-antibody reaction. Next, a secondary antibody to which a label substance 307 has bound (hereinafter referred to as a "labeled antibody 308") and the antigen 306 are allowed to bind through an antigen-antibody reaction. As a result, a composite 310 is obtained in which the magnetic-particle-immobilized antibody 305 and the labeled antibody 308 have bound to the antigen 306.

A signal which is based on the label substance 307 of the labeled antibody 308 that has bound to the composite 310 is detected, and an antigen concentration is measured in accordance with the amount of detected signal. Examples of the label substance 307 include enzymes (e.g., peroxidase, alkaline phosphatase, and luciferase), chemiluminescent substances, electrochemiluminescent substances, and fluorescent substances. In accordance with each such label substance 307, dye, luminescence, fluorescence, or other signals are detected.

In this series of reactions, in order to obtain the composite 310 as the reaction product, separation needs to be effected between unreacted substance in the analyte, substance that has non-specifically adsorbed to the magnetic particles or the like, and unreacted substance which was not involved in the formation of the composite 310 (e.g., the labeled antibody 308). This separation is called B/F separation (Bound/Free Separation). A B/F separation process is similarly required also in immunoassay techniques based on competitive assays and in genetic detection techniques based on hybridization. Examples of not using magnetic particle may include the use of: a ligand which is immobilized through physisorption to a solid phase composed of polystyrene, polycarbonate, or other materials, a ligand which is immobilized to a solid phase via a chemical bond, a ligand which is immobilized to the surface of a metal substrate composed of gold or the like (e.g., being immobilized by using a self-assembled monolayer (SAM)), and so on.

In order to perform adequate B/F separation, it is preferable to wash magnetic particles including the composite 310 multiple times with a wash solution. Specifically, first, from the reaction solution that contains the composite 310, the unreacted antigen 306, the labeled antibody 308, and the like, only the reaction solution is removed while keeping the composite 310 containing the magnetic particles captured with a magnet Thereafter, a wash solution is added and the composite 310 is washed, and the wash solution is removed. By repeating such washing multiple times, a B/F separation can be attained such that the unreacted substance and the non-specifically adsorbed substance are sufficiently removed.

Conventionally, a maneuver involving such multiple washes may be manually performed by an operator using analysis equipment, or achieved by a large-sized analysis apparatus with a complicated mechanism. Therefore, there has been a desire for a technique that achieves multiple washes in an easier manner.

By using a substrate for sample analysis as disclosed in Patent Document 1, the inventors have investigated into a technique that enables multiple wash processes, thus arriving at a novel substrate for sample analysis, sample analysis device, sample analysis system, and program for a sample analysis system. A substrate for sample analysis, a sample analysis device, a sample analysis system, and a program for a sample analysis system according to one aspect of the present application are as follows.

[Item 1] A substrate for sample analysis on which transfer of a liquid is to occur with rotational motion, the substrate for sample analysis comprising:
 a substrate having a rotation axis;
 a first chamber being located in the substrate and having a first space for retaining a liquid;
 a second chamber being located in the substrate and having a second space for retaining the liquid to be discharged from the first chamber; and
 a first channel being located in the substrate and having a path connecting the first chamber and the second chamber, the first channel being capable of being filled via capillary action with the liquid retained in the first space, wherein,
 the first space of the first chamber includes a first portion and a second portion, and a coupling portion being located between the first portion and the second portion and coupling the first portion and the second portion;
 the substrate has a wall portion partitioning the first portion and the second portion of the first space from each other;
 the second chamber is more distant from the rotation axis than is the first portion of the first chamber;
 the coupling portion of the first space is closer to the rotation axis than is the wall portion of the substrate; and
 the first channel is connected to the first portion of the first space.

[Item 2] The substrate for sample analysis of item 1, wherein a distance from the rotation axis to a position on the first portion at which the first channel is connected is longer than a distance from the rotation axis to a point on the wall portion that is the closest to the rotation axis.

[Item 3] The substrate for sample analysis of item 1 or 2, wherein the first portion of the first space includes a portion located outward of a circular arc which is centered around the rotation axis and whose radius is a line segment connecting the rotation axis and a point on the wall portion that is the closest to the rotation axis.

[Item 4] The substrate for sample analysis of any of items 1 to 3, wherein the second portion of the first space includes a portion located outward of a circular arc which is centered around the rotation axis and whose radius is a line segment connecting the rotation axis and a point on the wall portion that is the closest to the rotation axis.

[Item 5] The substrate for sample analysis of item 3, wherein the second portion of the first space includes a portion which is more distant from the rotation axis than is the first portion.

[Item 6] The substrate for sample analysis of any of items 1 to 5, wherein a portion of the first portion of the first space that is, as viewed from a direction which is parallel to the rotation axis, located outward, of a circle which is centered around the rotation axis and whose radius is a line segment connecting the rotation axis and a point on the wall portion that is the closest to the rotation axis is ½ or less in volumetric capacity to that of the first space.

[Item 7] The substrate for sample analysis of any of items 1 to 6, wherein the second space is greater in volumetric capacity than a portion of the first portion of the first space that is, as viewed from a direction which is parallel to the rotation axis, located outward of a circle which is centered around the rotation axis and whose radius is a line segment connecting the rotation axis and a point on the wall portion that is the closest to the rotation axis.

[Item 8] The substrate for sample analysis of any of items 1 to 7, further comprising:
a third chamber being in the substrate located more distant from the rotation axis than is the second chamber and having a third space for retaining of the liquid to be discharged from the second chamber; and
a second channel being located in the substrate and having a path connecting the second chamber and the third chamber, the second channel capable of being filled via capillary action with the liquid that is retained in the second space.

[Item 9] The substrate for sample analysis of item 8, wherein,
the second channel includes a first bent portion which is convex toward an opposite side from the rotation axis and a second bent portion which is convex toward the rotation axis, the first bent portion being located between the second bent portion and the second chamber;
a distance from the rotation axis to the third chamber is longer than a distance from the rotation axis to an apex of the first bent portion; and
a distance from the rotation axis to a liquid surface of the liquid that is retained in the third chamber as created by a centrifugal force due to rotation of the substrate is longer than a distance from the rotation axis to an apex of the second bent portion.

[Item 10] The substrate for sample analysis of item 9, where, the first channel includes a first bent portion which is convex toward an opposite side from the rotation axis and a second bent portion which is convex toward the rotation axis, the first bent portion being located between the second bent portion and the first chamber;
a distance from the rotation axis to the second chamber is longer than a distance from the rotation axis to an apex of the first bent portion; and
a distance from the rotation axis to a liquid surface of the liquid that is retained in the first chamber as created by a centrifugal force due to rotation of the substrate is longer than a distance from the rotation axis to an apex of the second bent portion.

[Item 11] The substrate for sample analysis of any of items 1 to 10, further comprising a magnet located near the second chamber.

[Item 12] A sample analysis system comprising:
the substrate for sample analysis of item 11; and
a sample analysis device, including
a motor to rotate the substrate for sample analysis around the rotation axis in a state where the rotation axis is inclined at an angle which is greater than 0° but not more than 90° with respect to the direction of gravity,
a rotation angle detection circuit to detect an angle of a shaft of the motor,
a drive circuit to control rotation and a stopping angle of the motor based on a result of detection by the rotation angle detection circuit, and
a control circuit including an arithmetic unit, a memory, and a program which is stored in the memory and executable by the arithmetic unit, to control based on the program an operation of the motor, the rotation angle detection circuit, the origin detector, and the drive circuit,
wherein,
when the substrate for sample analysis with the first chamber being filled with the liquid is placed on a turntable of the sample analysis device,
the program comprises the processes of:
(a) stopping the substrate for sample analysis at a predetermined first angle to allow a portion of the liquid to move within the first chamber based on gravity, fill at least a part of the first portion of the first chamber with the portion of the liquid, and transfer another portion of the liquid to the first channel via capillary action,
(b) rotating the sample is substrate at a rate causing a centrifugal force which is stronger than a capillary force acting on the liquid filling the first channel to, with a centrifugal force due to rotation of the substrate, measure out a portion of the liquid in the first portion, move excess liquid to the second portion to thereby allow the remaining liquid to be retained in the second portion, and move the measured portion of the liquid in the first portion to the second chamber through the first channel,
(c) stopping the substrate for sample analysis at a predetermined second angle to allow a portion of the remaining liquid to move within the first chamber based on gravity, fill at least a part of the first portion of the first chamber with the portion of the remaining liquid, and transfer another portion of the remaining liquid to the first channel via capillary action, and
(d) rotating the sample analysis substrate at a rate causing a centrifugal force which is stronger than a capillary force acting on the liquid filling the first channel to, with a centrifugal force due to rotation of the substrate, measure out a portion of the remaining liquid in the first portion, move excess liquid to the second portion to thereby allow the superfluous liquid to be retained in the second portion, and move measured portion of the remaining liquid in the first portion to the second chamber through the first channel.

[Item 13] The sample analysis system of item 12, further comprising, between the process (b) and the process (c), the processes of:

(e) stopping the substrate for sample analysis at a predetermined third angle to transfer a portion of the liquid in the second chamber to the second channel via capillary action; and (f) rotating the sample analysis substrate at a rate causing a centrifugal force which is stronger than a capillary force acting on the liquid filling the second channel to, with a centrifungal force due to rotation of the substrate, move the liquid in the second chamber to the third chamber through the second channel.

[Item 14] The sample analysis system of item 13, further comprising, after the process (d), the processes of:

(g) stopping the sub for sample analysis at a predetermined fourth angle to transfer a portion of the liquid in the second chamber to the second channel via capillary action; and (h) rotating the sample analysis substrate at a rate causing a centrifugal force which is stronger than a capillary force ting on the liquid filling the second channel to, with a centrifugal force due to rotation of the substrate, move the liquid in the second chamber to the third chamber through the second channel.

[Item 15] The sample analysis system of item 12, wherein, in at least one of the processes (a) and (b), after stopping rotation of the substrate for sample analysis, the substrate is allowed to alternately rotate clockwise or counterclockwise by a predetermined angle.

[Item 16] A sample analysis device comprising:
a motor to rotate the substrate for sample analysis of item 8 around the rotation axis in a state where the rotation axis is inclined at an angle which is greater than 0° but not more than 90° with respect to the direction of gravity,
a rotation angle detection circuit to detect an angle of a shaft of the motor,
a drive circuit to control rotation and a stopping angle of the motor based on a result of detection by the rotation angle detection circuit, and
a control circuit including an arithmetic unit, a memory, and a program which is stored in the memory and executable by the arithmetic unit, to control based on the program an operation of the motor, the rotation angle detection circuit, and the drive circuit,
wherein,
when the substrate for sample analysis with the first chamber being filled with the liquid is placed on a turntable of the sample analysis device,
the program comprises the processes of:
(a) stopping the substrate for sample analysis at a predetermined first angle to allow a portion of the liquid to move within the first chamber based on gravity, fill at least a part of the first portion of the first chamber with the portion of the liquid, and transfer another portion of the liquid to the first channel via capillary action,
(b) rotating the sample analysis substrate at a rate causing a centrifugal force which is stronger than a capillary force acting on the liquid filling the first channel to, with a centrifugal force due to rotation of the substrate, measure out a portion of the liquid in the first portion, move excess liquid to the second portion to thereby allow the remaining liquid to be retained in the second portion, and move the measured portion of the liquid in the first portion to the second chamber through the first channel, (c) stopping the substrate for sample analysis at a predetermined second angle to allow a portion of the remaining liquid to move within the first chamber based on gravity, fill at least a part of the first portion of the first chamber with the portion of the remaining liquid, and transfer another portion of the remaining liquid to the first channel via capillary action, and (d) rotating the sample analysis substrate at a rate causing a centrifugal force which is stronger than a capillary force acting on the liquid filling the first channel to, with a centrifugal force due to rotation of the substrate, measure out a portion of the remaining in the first portion, move excess liquid to the second portion to thereby allow the superfluous liquid to be retained in the second portion, and move the measured portion of the remaining liquid in the first portion to the second chamber through the first channel.

[Item 17] A program for a sample analysis system comprising:
the substrate for sample analysis of item 8; and
a sample analysis device, including
a motor to rotate the substrate for sample analysis around the rotation axis in a state where the rotation axis is inclined at an angle which is greater than 0° but not more than 90° with respect to the direction of gravity,
a rotation angle detection circuit to detect an angle of a shaft of the motor,
a drive circuit to control rotation and a stopping angle of the motor based on a result of detection by the rotation angle detection circuit, and
a control circuit including an arithmetic unit, a memory, and a program which is stored in the memory and executable by the arithmetic unit, to control based on the program an operation of the motor, the rotation angle detection circuit, the origin detector, and the drive circuit,
wherein,
when the substrate for sample analysis with the first chamber being filled with the liquid is placed on a turntable of the sample analysis device,
the program comprises the processes of:
(a) stopping the substrate for sample analysis at predetermined first angle to allow a portion of the liquid to move within the first chamber based on gravity, fill at least a part of the first portion of the first chamber with the portion of the liquid, and transfer another portion of the liquid to the first channel via capillary action,
(b) rotating the sample analysis substrate at a rate causing a centrifugal force which is stronger than a capillary force acting on the liquid filling the first channel to, with a centrifugal force due to rotation of the substrate, measure out a portion of the liquid in the first portion, move excess liquid to the second portion to thereby allow the remaining liquid to be retained in the second portion, and move the measured portion of the liquid in the first portion to the second chamber through the first channel,
(c) stopping the substrate for sample analysis at a predetermined second angle to allow a portion of the remaining liquid to move within the first chamber based on gravity, fill at least a part of the first portion of the first chamber with the portion of the remaining liquid, and transfer another portion of the remaining liquid to the first channel via capillary action, and
(d) rotating the sample analysis substrate at a rate causing a centrifugal force which is stronger than a capillary force acting on the liquid filling the first channel to, with a centrifugal force due to rotation of the substrate, measure out a portion of the remaining liquid in the first portion, move excess liquid to the second portion to thereby allow the superfluous liquid to be retained in the second portion, and move the measured portion of the remaining liquid in the first portion to the second chamber through the first channel.

Hereinafter, with reference to the drawings, the substrate for sample analysis, sample analysis device, sample analysis system, and program for a sample analysis system according to the present embodiment will be described in detail. The substrate for sample analysis, sample analysis device, sample analysis system, and program for a sample analysis system according to the present embodiment are able to measure out a certain amount of a liquid that is retained in one chamber, and transfer it to different chambers over multiple times. Although the embodiment will illustrate the liquid(s) to be a wash solution(s), the liquid(s) may be any of various liquids for use in sample analysis, without being limited to a wash solution(s).

Figure 2A:
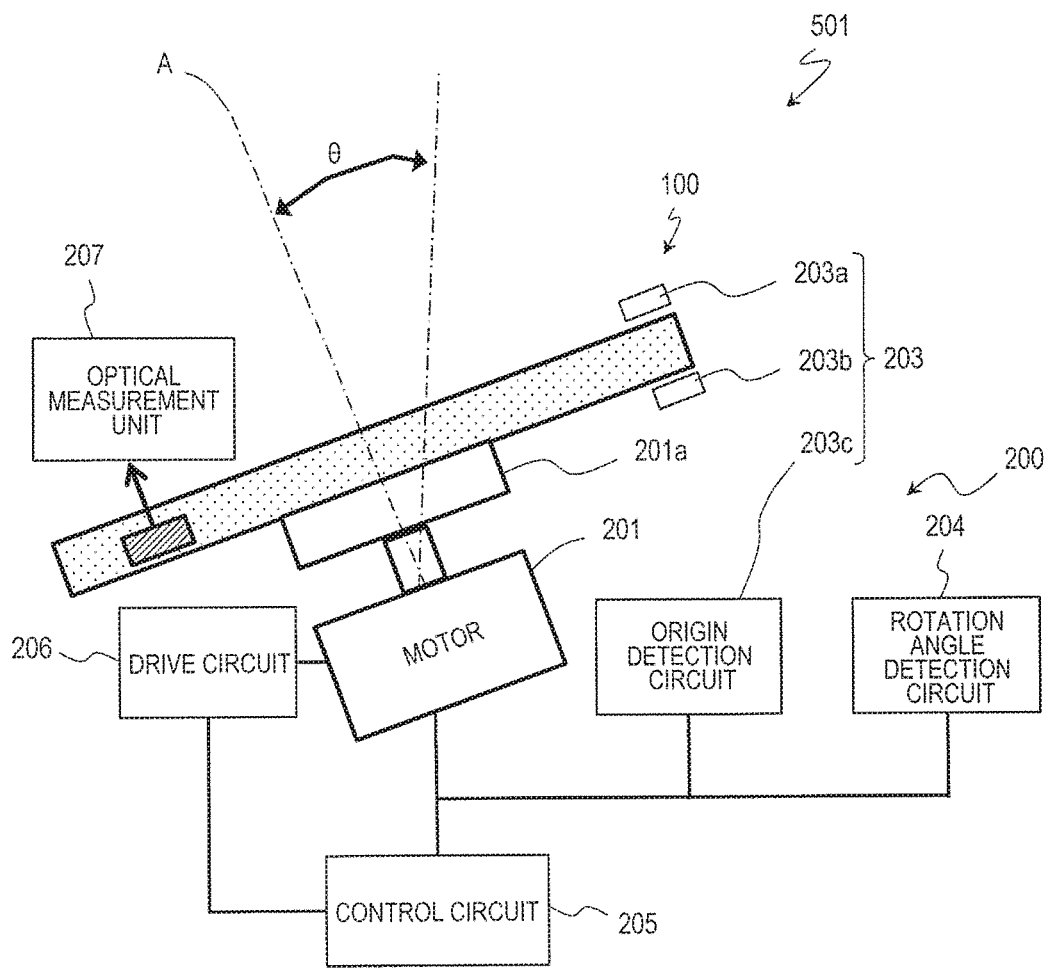
FIG. 2A A schematic diagram showing an exemplary construction of a sample analysis system according to embodiment.

FIG. 2A is a schematic diagram showing an overall construction of the sample analysis system 501. The sample analysis system 501 includes a substrate 100 for sample analysis and a sample analysis device 200.

(Construction of the Sample Analysis Device 200)

The sample analysis device 200 includes a motor 201, an origin detector 203, a rotation angle detection circuit 204, a control circuit 205, a drive circuit 206, and an optical measurement unit 207.

The motor 201 includes a turntable 201a and a shaft A which is tilted from the direction of gravity at an angle θ which is greater than 0° but not more than 90° with respect to the direction of gravity, and rotates the substrate 100 for sample analysis placed on the turntable 201a around the shaft A. Since the shaft A is tilted, not only a centrifugal force due to rotation but a gravity-based transfer can also be utilized for causing a transfer of any liquid in the substrate 100 for sample analysis. The angle of tilt of the shaft A with respect to the direction of gravity is preferably 5° or more, more preferably not less than 10° and not more than 45°, and still more preferably not less than 20° and not more than 30°. The motor 201 may be a DC motor, a brushless motor, an ultrasonic motor, or the like, for example.

Figure 2B:
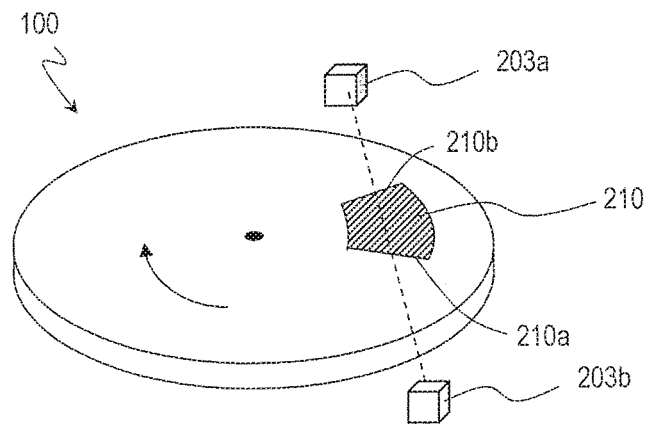
FIG. 2B A schematic diagram showing an exemplary construction for detecting an origin of a substrate for sample analysis in a sample analysis system.

The origin detector 203 detects an origin of the substrate 100 for sample analysis which is attached to the motor 201. For example, as shown in FIG. 2B, the origin detector 203 includes a light source 203a, a photodetector 203b, and an origin detection circuit 203c, and is disposed so that the substrate 100 for sample analysis comes between the light source 203a and the photodetector 203b. For example, the light source 203a may be a light-emitting diode, and the photodetector 203b may be a photodiode. The substrate 100 for sample analysis has a marker 210 at a specific position. The marker 210 has a light shielding ability to shade at least part of the light which exits the light source 203a, for example. The substrate 100 for sample analysis has a small transmittance (e.g. 10% or ss) in the region of the marker 210, and a large transmittance (e.g. 60% or more) in the region other than the marker 210.

As the substrate 100 for sample analysis is rotated by the motor 201, the photodetector 203b outputs a detection signal which is in accordance with the amount of incident light on the origin detection circuit 203c. Depending on the direction of rotation, the detection signal may increase or decrease at an edge 210a and at an edge 210b of the marker 210. The origin detection circuit 203c detects a decrease in the amount of detected light and outputs it as an origin signal, for example, while the substrate 100 for sample analysis is rotating clockwise as indicated by the arrow. In the present specification, the position of the edge 210a of the marker 210 will be regarded as the origin position of the substrate 100 for sample analysis (i.e., a reference angular position of the substrate 100 for sample analysis). However, a position at any specific angle, as arbitrarily determined from the position of the edge 210a of the marker 210, might be defined as an origin. In the case where the marker 210 has a sector shape, with a central angle being smaller than the precision of angle detection that is required for sample analysis, the marker 210 itself may be regarded as the origin position.

The origin position is utilized by the sample analysis device 200 in acquiring information on the rotation angle of the substrate 100 for sample analysis.

The origin detector 203 may have any other construction. For example, a magnet for use in origin detection may be provided on the substrate 100 for sample analysis, and, instead of the photodetector 203b, the origin detector 203 may include a magnetism detector which detects magnetism of this magnet. Moreover, a magnet for use in capturing the magnetic particles, as described later, may also be utilized for origin detection. In the case where the substrate 100 for sample analysis is attachable to the turntable 201a only at a specific angle, the origin detector 203 may be omitted.

The rotation angle detection circuit 204 detects the angle of the shaft A of the motor 201. For example, the rotation angle detection circuit 204 may be a rotary encoder that is attached to the shaft A. In the case where the motor 201 is a brushless motor, the rotation angle detection circuit 204 may include a Hall generator that is provided on the brushless motor and a detection circuit which receives an output signal from the Hall generator and outputs the angle of the shaft A.

The drive circuit 206 rotates the motor 201. Specifically, based on an instruction from the control circuit 205, the substrate 100 for sample analysis is rotated clockwise or counterclockwise. Moreover, based on results of detection by the rotation angle detection circuit 204 and the origin detector 203 and on an instruction from the control circuit 205, stops swings or rotation of the substrate 100 for sample analysis.

The optical measurement unit 207 detects a signal (e.g., dye, luminescence, fluorescence, etc.) which is in accordance with the label substance 307 of the labeled antibody 308 that has bound to the composite 310 (FIG. 1) being retained on the substrate 100 for sample analysis.

The control circuit 205 is a CPU which is provided in the sample analysis device 200, for example. By executing a computer program that is loaded into a RAM (Random Access Memory; not shown), the control circuit 205 sends instructions to other circuitry in accordance with the procedure defined by the computer program. Upon receiving such an instruction, each circuit operates as will be described in the present specification, whereby the function of the respective circuit is realized. The instructions from the control circuit 205 are sent to the drive circuit 206, the rotation angle detection circuit 204, the optical measurement unit 207, and the like, as shown in FIG. 2A, for example. The procedure defined by the computer program is shown by a flowchart in the attached drawings.

Note that a RAM into which a computer program is loaded, i.e., a RAM storing a computer program, may be volatile or non-volatile. A volatile RAM is a RAM which in the absence of supplied power is unable to retain the information that is stored therein. For example, a dynamic random access memory (DRAM) is a typical volatile RAM. A non-volatile RAM is a RAM which is able to retain information without power being supplied thereto. For example, a magnetoresistive RAM (MRAM), a resistive random access memory (ReRAM), and a ferroelectric memory (FeRAM) are examples of non-volatile RAMS. In the present embodiment, a non-volatile RAM is preferably adopted. A volatile RAM and a non-volatile RAM are both examples of non-transitory, computer-readable storage media. Moreover, a magnetic storage medium such as a hard disk, and an optical storage medium such as an optical disc are also examples of non-transitory, computer-readable storage media. That is, a computer program according to the present disclosure may be recorded on various non-transitory computer-readable media, excluding any medium such as the atmospheric air (transitory media) that allows a computer program to be propagated as a radiowave signal.

In the present specification, tie control circuit 205 is described as a distinct component element from the rotation angle detection circuit 204 and the origin detection circuit 203c of the origin detector 203. However, these may be implemented by the same hardware. For example, in a serial or parallel manner, a CPU (computer) which is provided in the sample analysis device 200 may execute a computer program to function as the control circuit 205, a computer program to function as the rotation angle detection circuit 204, and a computer program to function as the origin detection circuit 203c of the origin detector 203. This allows the CPU to apparently operate as distinct component elements.

(Substrate 100 for Sample Analysis)

Figure 3A:
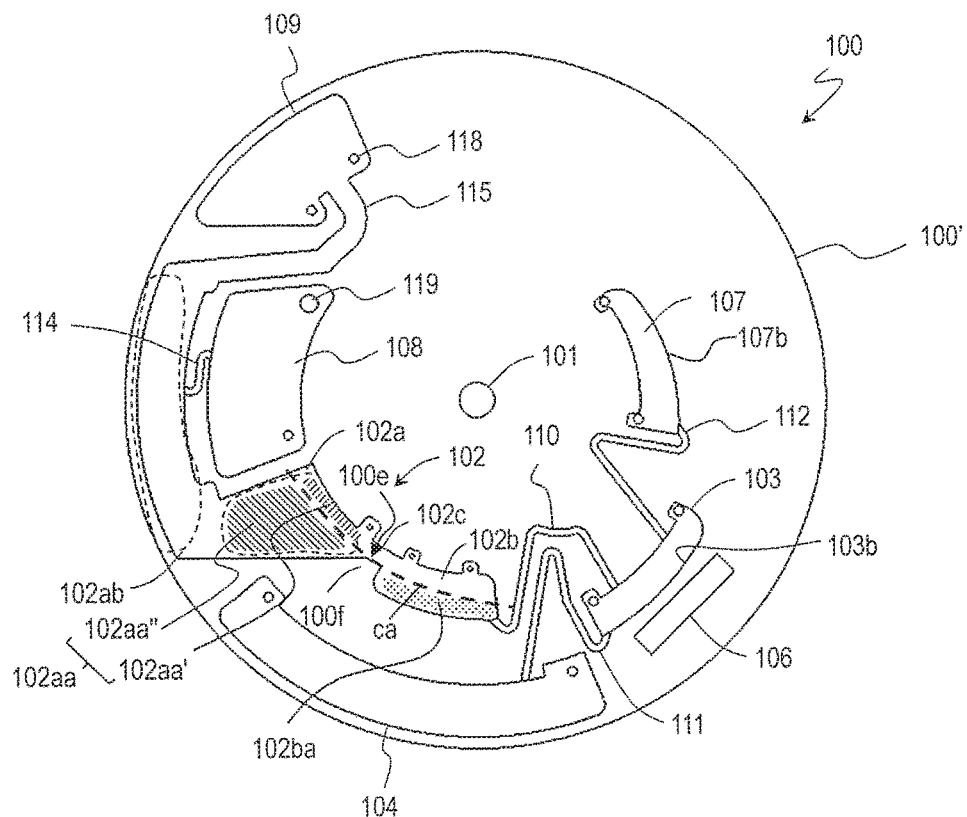
FIG. 3A A plan view showing an exemplary structure of a substrate for sample analysis.
Figure 3B:
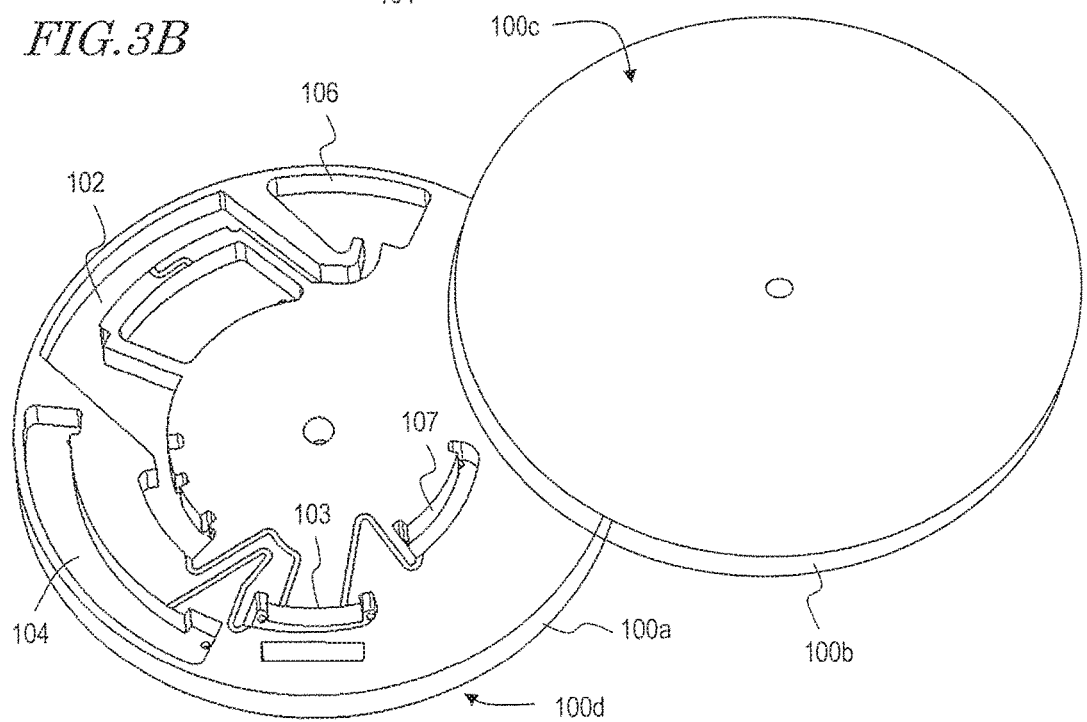
FIG. 3B An exemplary exploded perspective view of the substrate for sample analysis shown in FIG, 3A.

FIG. 3A and FIG. 3B are a plan view and an exploded perspective view of the substrate 100 for sample analysis. The substrate 100 for sample analysis includes a substrate 100' having a rotation axis 101 and a plate shape with a predetermined thickness along a direction which is parallel to the rotation axis. Although the substrate 100' of the substrate 100 for sample analysis has a circular shape in the present embodiment, it may alternatively be shaped as a polygon, an ellipse, a sector, or the like. The substrate 100' has two principal faces 100c and 100d. In the present embodiment, the principal face 100c and the principal face 100d are parallel to each other, and the thickness of the substrate 100' as defined by an interspace between the principal face 100c and the principal face 100d is constant irrespective of position within the substrate 100'. However, the principal faces 100c and 100d do not need to be parallel. For example, the two principal faces may be partly non-parallel or parallel, or be entirely non-parallel. Moreover, at least one of the principal faces 100c and 100d of the substrate 100' may have a structure with recesses or protrusions. The substrate 100 for sample analysis includes a first chamber 102, a second chamber 103, a third chamber 104, a first storage chamber 108, a second storage chamber 109, and a reaction chamber 107, each located in the substrate 100'. Unless otherwise specified below, there is no particular limitation as to the shape of each chamber, which may have any arbitrary shape. Except for the first chamber 102, each chamber includes a space which is generally defined by an upper face and a lower face that are parallel to the two principal faces of the substrate 100' and four side faces located. therebetween. Any two adjoining faces among the upper face, the lower face, and the side faces may not be parted by a clearly defined ridge. For example, the shape of each chamber may be an oblate sphere or a spheroid.

Furthermore, the substrate 100 for sample analysis includes a first channel 110, a second channel 111, a third channel 112, a fourth channel 114, and a fifth channel 115, each located in the substrate 100'. The first channel 110 interconnects the first chamber 102 and the second chamber 103. The second channel 111 interconnects the second chamber 103 and the third chamber 104. The third channel 112 interconnects the reaction chamber 107 and the second chamber 103. The fourth channel 114 interconnects the first storage chamber 108 and the first chamber 102. The fifth channel 115 interconnects the first chamber 102 and the second storage chamber 109.

The transfer of liquids between the chambers by way of the channels can attained by various methods. For example, a gravity-based transfer and a transfer based on a capillary force and a centrifugal force associated with rotation can be utilized. Hereinafter, these two transfer methods will be described in outline.

For example, the substrate 100 for sample analysis is supported so that its shaft A is tilted in a range which is greater than 0 degrees but not more than 90 degrees with respect to the vertical direction. Then, by changing the rotation angular position of the substrate 100 for sample analysis, the chamber from which the transfer occurs and in which a liquid exists is allowed to be disposed at a higher position than the chamber that is the destination of transfer. To be "high" means being located more upward along the vertical direction. As result of this, the liquid can be transferred to the other chamber by utilizing gravity. In this case, the channel which couples between the chambers is not a capillary channel. A "capillary channel" would mean a channel with a narrow space which can be filled inside with a liquid via capillary action.

Moreover, a capillary channel may also be utilized in transferring a liquid to another chamber. A liquid transfer through a capillary channel will be described with respect to an exemplary construction including chamber A and chamber B, which are not capillary tube spaces, and a capillary channel, which connects between chamber A and chamber B. When a liquid being retained in chamber A comes in contact with an opening that defines an interconnection between chamber A and the capillary channel, the liquid is pulled into the capillary channel by a capillary force, whereby the interior of the channel becomes filled with the liquid. However, when the substrate 100 for sample analysis is rotated with such a number of revolutions (including also a stopped state) as will apply to the liquid inside the channel a centrifugal force which is equal to or less than the capillary force that is acting on the liquid inside channel, then the liquid in the capillary channel will remain in the capillary tube space, without being transferred to chamber B. In order to fill the interior of the capillary channel with the liquid thus via capillary action, an air hole (air pathway between the external environment and the chamber) must be provided at the chamber B side, i.e., at the outlet side of the capillary channel. Moreover, in order to effect a liquid transfer via capillary action within the closed space defined by chamber A, chamber B, and the capillary channel, an air hole must also be provided at the chamber A side, i.e., at the inlet side of the capillary channel, as dictated by the relationship between air pressures inside the chambers and the channel. Then, assuming that chamber B is disposed more distant from the rotation axis than is chamber A, from a state in which this capillary channel is filled with the liquid, the substrate 100 for sample analysis may be rotated with such a number of revolutions as will apply a centrifugal force which is greater than the capillary force that is acting on the liquid inside the capillary channel, whereby the liquid in chamber A can be transferred to chamber B with this centrifugal force.

In the case where a liquid is to be transferred with a capillary force or a centrifugal force due to rotation, for example, a substrate 100 for sample analysis having a diameter of 60 mm can be rotated in a range from 100 rpm to 8000 rpm. The rotation speed is determined in accordance with the shape of each chamber and channel, the physical properties of liquids, the timing of transfers of liquids and treatments, and the like.

In the present embodiment, the substrate 100' of the substrate 100 for sample analysis is composed of a base substrate 100a and a cover substrate 100b. The respective spaces of the first chamber 102, the second chamber 103, the third chamber 104, the first storage chamber 108, the second storage chamber 109, and the reaction chamber 107 are formed within the base substrate 100a, and as the cover substrate 100b covers over the base substrate 100a, a top and a bottom of each space are created. In other words, these spaces are defined by inner surfaces of the substrate 100'. The first channel 110, the second channel 111, the third channel 112, the fourth channel 114, and the fifth channel 115 are also formed in the base substrate 100a, and as the cover substrate 100b covers over the base substrate 100a, a top and a bottom of the respective channel space are created. In the present embodiment, the base substrate 100a and the cover substrate 100b are utilized respectively as an upper face and a lower face. The substrate 100' may be formed of a resin which may be acrylic, polycarbonate, polystyrene, or the like.

As has been described with reference to FIG. 1, the reaction chamber 107 is a reaction field in which the magnetic-particle-immobilized antibody 305, an analyte containing the antigen 306, and the labeled antibody 308 are allowed to react and form the composite 310. There is no particular limitation as to the shape of the reaction chamber 107. The interconnection between the reaction chamber 107 and the third channel 112 is preferably provided on, among side faces of the reaction chamber 107 that are located in a parallel direction to the rotation axis 101: a side face (outermost side face) that is the farthest from the rotation axis 101; or a side face adjoining the outermost side face, at a position that encompasses the position of connection with the outermost side wall. The reason is that, when transferring the liquid in the reaction chamber 107 to the second chamber 103, this can restrain residual liquid in the reaction chamber 107. The example of FIG. 3A illustrates a construction where interconnection between the reaction chamber 107 and the third channel 112 is on the outermost side face, at a boundary position with one of the side faces adjoining the outermost side face.

In the present embodiment, the substrate 100 for sample analysis includes the reaction chamber 107 as a reaction field where the composite 310 is allowed to form. Various means may be adopted in transferring the magnetic-particle-immobilized antibody 305, an analyte containing the antigen 306, and the labeled antibody 308 to the reaction chamber 107. For example, mixed solution in which the magnetic-particle-immobilized antibody 305, the analyte containing the antigen 306, and the labeled antibody 308 have been previously mixed may be measured out, and the mixed solution may be injected into the reaction chamber 107 in the substrate 100 for sample analysis. Moreover, the substrate 100 for sample analysis may include chambers respectively retaining the magnetic-particle-immobilized antibody 305, the analyte containing the antigen 306, and the labeled antibody 308, and a channel (e.g., a capillary channel) via which each chamber and the reaction chamber 107 are coupled. In this case, the magnetic-particle-immobilized antibody 305, the analyte containing the antigen 306, and the labeled antibody 308 may be measured out into the respective chambers; and the magnetic-particle-immobilized antibody 305, the analyte containing the antigen 306, and the labeled antibody 308 having been injected into the respective chambers may be transferred to the reaction chamber 107 and mixed in the reaction chamber 107 to form the composite 310. Moreover, the magnetic-particle-immobilized antibody 305 and the labeled antibody 308 may be dried (hereinafter referred to as "dried reagents"). In this case, for example, the dried reagents may be retained in the reaction chamber 107, and dissolved by a liquid containing an analyte solution containing the antigen 306 to form the composite 310. Moreover, a dried reagent retained in a certain chamber during measurement may be dissolved by a predetermined solution, and an analyte solution containing the antigen 306 may be mixed in the reaction chamber 107, thereby allowing the composite 310 to form.

The solution containing the composite 310 is transferred to the second chamber 103 via the third channel 112.

In the second chamber 103, B/F separation is to be effected for the solution containing the composite 310. For this purpose, the substrate 100 for sample analysis includes a magnet 106. The second chamber 103 is more distant from the rotation axis 101 than are the reaction chamber 107 and a portion 102ba of the first chamber 102, which will be described later.

Although there is no particular limitation as to the shape of the second chamber 103, the interconnection between the second chamber 103 and the second channel 111 1s preferably provided on, among side faces of the second chamber 103 that are located in a parallel direction to the rotation axis 101: a side face (outermost side face) that is the farthest from the rotation axis 101; or a side face adjoining the outermost side face, at a position that encompasses the position of connection with the outermost side wall. The reason is that, when transferring the liquid in the second chamber 103 to the third chamber 104, this can restrain residual liquid in the second chamber 103. Note that the example of FIG. 3A illustrates a construction where the interconnection between the second chamber 103 and the second channel 111 is on the outermost side face, at a boundary position with one of the side faces adjoining the outermost side face.

Moreover, the interconnection between the second chamber 103 and the third channel 112 is preferably provided on, among side faces of the second chamber 103 that are located in a parallel direction to the rotation axis 101: a side face that is the closest to the rotation axis 101 (innermost side face); or a side face adjoining the innermost side face, at a position that encompasses the position of connection with the innermost side wall. The example of FIG. 3A illustrates a construction where the interconnection between the second chamber 103 and the third channel 112 is at a part of the outermost side face.

In the substrate 100 for sample analysis, the magnet 106 is located near the space of the second chamber 103. More specifically, the magnet 106 is disposed, among the four side faces of the second chamber 103, near the side face 103b that is the farthest m the rotation axis 101. The magnet 106 may be configured to be capable of being attached or detached in adaptation with B/F separation, or undetachably attached to the substrate 100 for sample analysis.

The positioning of the magnet 106 in the substrate 100 for sample analysis is not limited to a position near the side face 103b of the second chamber 103. So long as the magnet 106 is able to capture the magnetic particles onto the wall surface of the second chamber 103, the magnet 106 may be disposed at any other position. For example, the magnet 106 may be disposed at any position near the upper face or the lower face other than the side face 103b of the second chamber 103. In other words, so long as the magnetic particles can be captured by the magnet 106 onto the wall surface of the third chamber 104, there is no particular limitation as to its position.

In the case where the magnet 106 is configured to be detachable, for example, the substrate 100' has a receptacle in which the magnet 106 can be accommodated. For example, as shown in FIG, 3C, the substrate 100' may have a dented receptacle 120 with an opening 120a in the principal face 100c. The receptacle 120 has a space in which the magnet 106 can be accommodated. By inserting the magnet 106 through the opening 120aa into the receptacle 120, the magnet 106 becomes mounted to the substrate 100'. The opening 120a of the receptacle 120 may be made in the principal face 100d, or in a side face that is located between the two principal faces 100c and 100d.

Moreover, the magnet 106 may be provided on the sample analysis device 200. For example, the sample analysis device 200 may include a turntable 201a having a magnet 106. In this case, as the substrate 100 for sample analysis is placed at the turntable 201a, the magnet 106 becomes disposed at a position where it is able to capture the magnetic particles, e.g., near the side face 103b of the third chamber 104.

As another example of providing the magnet 106 on the sample analysis device 200, for example, the sample analysis device 200 may include a driving mechanism which moves the magnet 106 and the magnet 106. In this case, the substrate 100 for sample analysis may have a receptacle in which to retain the magnet 106, and in accordance with B/F separation, the driving mechanism may insert the magnet 106 into the receptacle of the substrate 100 for sample analysis or take the magnet 106 out of the receptacle.

The first storage chamber 108 holds a wash solution which is used in the washing during B/F separation. As will be described in detail below, the sample analysis system 501 of the present embodiment is able to wash the composite 3100 multiple times at B/F separation. Therefore, the first storage chamber 108 is able to retain a volume of wash solution that is adapted to the number of washes.

The first chamber 102 retains the entire wash solution that has been held in the first storage chamber 108, and measures out a predetermined amount of wash solution to be used in a single wash. For this purpose, the space of the first chamber 102 includes a second portion 102a, a first portion 102b, and a coupling portion 102c connecting the second portion 102a and the first portion 102b.

In the present embodiment, a part of the second portion 102a and the first portion 102b are generally disposed along a circumferential direction around the rotation axis 101. Between the second portion 102a and the first portion 102b is a wall portion 100f that is composed of an inner surface of the substrate 100'. The wall portion 100f partitions the second portion 102a and the first portion 102b from each other. The coupling portion 102c is in the same radial direction as the wall portion 100f of the substrate 100', and located closer to the rotation axis 101 than is the wall portion 100f. The coupling portion 102c is never filled with a liquid via capillary action, but allows a liquid to move between the first portion 102b and the second portion 102a based on gravity.

The first portion 102b includes a portion 102ba that is located outward of (i.e., distant from the rotation axis 101) a circular arc ca which is centered around the rotation axis 101 and whose radius is a line segment connecting the rotation axis 101 and a point 100e on the wall portion 100f that is the closest to the rotation axis. This portion 102ba makes it possible to measure out a predetermined amount of wash solution to be used in a single wash.

Moreover, the distance from the rotation axis to the position on the first portion 102b at which the first channel 110 is connected is longer than the distance from the rotation axis 101 to the point 100e on the wall portion 100f that is the closest to the rotation axis. Therefore, the wash solution which has been measured out by the portion 102ba can be transferred from the first channel 110 to the second chamber 103 with a centrifugal force due to rotation.

In the present embodiment, the second portion 102a of the space of the first chamber 102 includes a side portion 102aa and a bottom portion 102ab. Along a circumferential direction around the rotation axis 101, the side portion 102aa is present by the side of the first storage chamber 108. The bottom portion 102ab is more distant from the rotation axis 101 than is the first storage chamber 108. Moreover, a part of the side portion 102aa and a whole of the bottom portion 102ab of the second portion 102a are more distant from the rotation axis 101 than is the first portion 102b.

Preferably, the side portion 102aa includes: a portion 102aa' which is closer to the rotation axis 101 than is the circular arc ca; and a portion 102aa" which is located outward of the circular arc ca. As described above, the portion 102aa' is adjacent to the first portion 102b along a circumferential direction, and connects to the coupling portion 102c.

Within the second portion 102a of the first chamber 102, the portions which are located outward of the circular arc ca (i.e., distant from the rotation axis 101), that is, the portion 102aa" and the bottom portion 102ab, preferably have a total volumetric capacity which is greater than the entire amount of wash solution to be retained in the first storage chamber 108.

Since the space of the first chamber 102 includes the bottom portion 102ab, in a state where the substrate 100 for sample analysis is stopped at a predetermined angle, a portion of the wash solution that has been held in the first storage chamber 108 fills the fourth channel 114 via capillary action. Then, as the substrate 100 for sample analysis is rotated with the fourth channel 114 being filled with the wash solution, the resultant centrifugal force causes the wash solution in the first storage chamber 108 to be transferred via the fourth channel 114 to the bottom portion 102ab.

When the substrate 100 for sample analysis is retained at a predetermined angle, based on gravity, a portion of the wash solution that has been transferred to the bottom portion 102ab of the first chamber 102 flows through the coupling portion 102c to the first portion 102b, and fills at least a part of the first portion 102b. Thereafter, as the substrate 100 for sample analysis is rotated, a centrifugal force acts on the wash solution filling the first portion 102b and a superfluous amount out of the wash solution retained in the first portion 102b is returned to the second portion 102a, so that the circular arc ca whose radius is a line segment connecting the rotation axis 101 and the point 100e on the wall portion 100f that is the closest to the rotation axis 101 (indicated by a broken line in FIG. 3A) will align with the liquid surface of the wash solution in the first portion 102b. As a result of this, a predetermined amount of wash solution is measured out.

A portion of the first portion 102b that is located outward of the circular arc ca whose radius is a line segment connecting the rotation axis 101 and the point 100e on the wall portion 100f that is the closest to the rotation axis 101 has a volumetric capacity which is ½ or less of the volumetric capacity of the first chamber 102. The details thereof are to be described below.

Although the present embodiment illustrates the second portion 102a to be of a construction in which a part of the side portion 102aa and the bottom portion 102ab are included, the second portion 102a may at least include a portion located outward of a circular arc which is centered around the rotation axis 101 and whose radius is a line segment connecting the rotation axis 101 and a point on the wall portion 100f that is the closest to the rotation axis 101.

The second chamber 103 provides a place in which to effect B/F separation. In a state where the substrate 100 for sample analysis is stopped at a predetermined angle, the third channel 112 becomes filled with a portion of a liquid containing the composite 310 and unreacted substance (hereinafter referred to as the reaction liquid) in the reaction chamber 107, via capillary action. Then, with the third channel 112 being filled with the reaction liquid, as the substrate 100 for sample analysis is rotated with such a number of revolutions as will apply a centrifugal force which is greater than the capillary force that is acting on the liquid inside the third channel 112, the resultant centrifugal force causes the reaction liquid in the reaction chamber 107 to be transferred via the third channel 112 to the second chamber 103.

When the reaction liquid is transferred to the second chamber 103, the composite 310 and the unreacted magnetic-particle-immobilized antibody 305 in reaction liquid (hereinafter, any allusion to both of these simultaneously will be made simply as the magnetic particles 311) are captured onto the side face 103b by a magnetic force of the magnet 106 disposed near the side face 103b. Moreover, in a state where the substrate 100 for sample analysis is stopped at a predetermined angle, the second channel 111 is filled with a portion of the reaction liquid (except for the magnetic particles 311 that have been captured by the magnet 106 onto the side face 103b) in the second chamber 103 via capillary action. From this state, as the substrate 100 for sample analysis is rotated with such a number of revolutions as will apply a centrifugal force which is greater than the capillary force that is acting on the liquid inside the second channel 111, the resultant centrifugal force causes the reaction liquid (except for the magnetic particles that have been captured by the magnet 106 onto the side face 103b) in the second chamber 103 to be transferred through the second channel 111 to the third chamber 104.

The certain amount of wash solution which has been measured out in the first chamber 102 fills the first channel 110 via capillary action, and thereafter, as the substrate 100 for sample analysis is rotated with such a number of revolutions as will apply a centrifugal force which is greater than the capillary force that is acting on the liquid inside the first channel 110, is transferred through the first channel 110 to the second chamber 103 by the resultant centrifugal force. For this reason, the second chamber 103 is greater in volumetric capacity than the portion of the first portion 102b of the first chamber 102 that is located outward of the circular arc.

The third chamber 104 stores the liquid which is discharged from the second chamber 103 via the second channel 111 with the resultant centrifugal force when the substrate 100 for sample analysis is rotated. For this reason, the third chamber 104 is more distant from the rotation axis 101 than is the second chamber 103.

The second storage chamber 109 stores a portion of the wash solution which had been retained in the first chamber 102 but was not used for washing. The first chamber 102 and the second storage chamber 109 are connected by the fifth channel 115.

The first chamber 102, the second chamber 103, the third chamber 104, the first storage chamber 108, the second storage chamber 109, and the reaction chamber 107 each have at least one air hole 118. As a result, the interior of each chamber is maintained at the environmental air pressure, so that each channel can control the liquid to be moved or stopped with the use of the capillary channel and the siphon structure. Moreover, an opening 119 through which to inject or discharge liquids such as an analyte solution, a reaction solution, or a wash solution may be made in the first storage chamber 108 and the reaction chamber 107.

In each chamber, the air hole 118 and the opening 119 are preferably disposed on the upper face, toward the side face that is near the rotation axis 101. This restrains, even when the substrate 100 for sample analysis rotates with each chamber being filled with a liquid, the air hole 118 and the opening 119 from coming in contact with the liquid to allow the liquid to move through the air hole 118 and the opening 119 to outside of the substrate 100 for sample analysis. The air hole 118 and the opening 119 may be provided on a side face portion of each chamber.

Moreover, the space of each chamber preferably has a convex portion protruding toward the rotation axis 101, with the air hole 118 and opening 119 being located in this convex portion. Such construction will allow the air hole 118 and the opening 119 in each chamber to be positioned as close to the rotation axis 101 along the radial direction as possible. Thus, the amount of liquid that can be retained in each chamber without coming in contact with the air hole 118 and the opening 119 when the substrate 100 for sample analysis has rotated, within the chamber space, any dead space that is not available to retain a liquid can be reduced.

Figure 4:
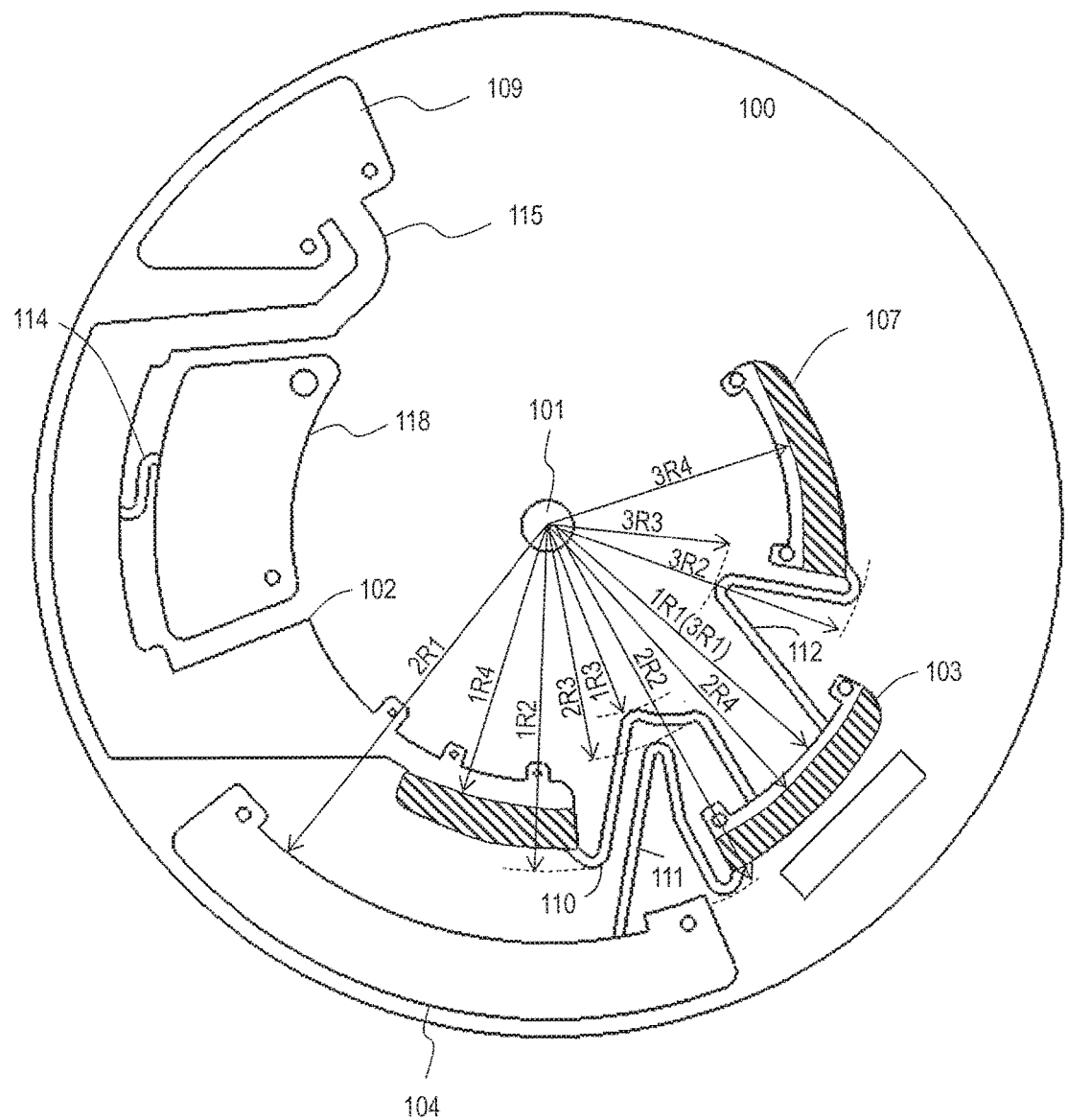
FIG. 4 A diagram showing an example of relative positioning between channels and chambers.

Next, with reference to FIG. 4, each channel will be described. The first channel 110, the second channel 111, the third channel 112, and the fourth channel 114 can filled inside with a liquid via capillary action. Specifically, via capillary action, the first channel 110, the second channel 111, the third channel 112, and the fourth channel 114 can be filled inside with the liquids filling the first chamber 102, the second chamber 103, the reaction chamber 107, and the first storage chamber 108, respectively. In other words, the first channel 110, the second channel 111, the third channel 112, and the fourth channel 114 are preferably capillary channels or capillary tubes.

For example, the first channel 110, the second channel 111, the third channel 112, and the fourth channel 114 may each have a width of 0.1 mm to 5 mm and a depth of 50 µm to 300 µm, or a width of 50 µm or more (preferably 50 µm to 300 µm) and a depth of 0.1 mm to 5 mm, in a cross section which is perpendicular to the direction that the channel extends. On the other hand, the fifth channel 115 and the connection point 100e have a large enough cross-sectional area to allow a liquid to move therethrough based on gravity.

Moreover, in the case where the aforementioned channels are capillary channels, hydrophilic treatment may be performed for the inner surfaces of the substrate 100' defining each channel, and for any inner surface near the interconnection of the chamber to which the channel is connected. The hydrophilic treatment will allow a large capillary force to act. The hydrophilic treatment can performed by coating the aforementioned inner surfaces with a nonionic-type, cation-type, anion-type, or amphoteric-type surfactant, performing a corona discharge treatment, or providing minute physical ruggednesses, and so on, for example (see Japanese Laid-Open Patent Publication No. 2007-3361, for example).

Moreover, it is preferable that the first channel 110, the second channel 111, and the third channel 112 can control liquid movements by the siphon principle. For this reason, the first channel 110, the second channel 111, and the third channel 112 each have a first bent portion and a second bent portion. The first bent portion has a shape which is convex toward the opposite side from the rotation axis 101, whereas the second bent portion has a shape which is convex toward the rotation axis 101. Regarding two chambers that are connected by a channel, the first bent portion is located between the second bent portion and the chamber that is closer to the rotation axis 101.

As used herein, the siphon principle means the liquid transfer being controlled based on a balance between the centrifugal force acting on the liquid due to rotation of the substrate 100 for sample analysis and capillary force within the channel. Specifically, an example where a liquid is transferred from the reaction chamber 107 to the second chamber 103, and further to the third chamber 104, will be described.

For example, in the case where the second channel 111 is a capillary channel which lacks siphon structure, in the course of a transfer from the reaction chamber 107 to the second chamber 103 via the third channel 112 based on a centrifugal force due to rotation of the substrate 100 for sample analysis, a liquid which has been transferred to the second chamber 103 will fill inside the second channel 111 because of a capillary force in the second channel 111. If rotation of the substrate 100 for sample analysis continues in this state, the liquid will not be retained in the second chamber 103, but will be transferred over to the third chamber 104 through the third channel 112. The rotation of the substrate 100 for sample analysis as referred to herein is based on a number of revolutions that allows a centrifugal force which is stronger than the capillary force in the second channel 111.

On the other hand, in the case where the second channel 111 has a siphon structure, a liquid which has been transferred from the reaction chamber 107 to the second chamber 103 will be drawn into the second channel 111 by a capillary force in the second channel 111. However, if rotation of the substrate 100 for sample analysis continues with such a number of revolutions as will apply a centrifugal force which is stronger than the capillary force in the second channel 111, then the second channel 111 will not be entirely filled with the liquid, since the centrifugal force is stronger than the capillary force acting on the liquid. In other words, the liquid will fill the second channel 111 only up to the same height as the distance from the rotation axis 101 of the liquid surface of the liquid existing in the second chamber 103. Then, if it is desired to transfer the liquid in the second chamber 103 to the third chamber 104, rotation of the substrate 100 for sample analysis may be effected with such a number of revolutions (including also halted rotation) as will apply a centrifugal force which is equal to or less than the capillary force in the second channel 111, whereby the second channel 111 will become entirely filled with the liquid due to the capillary force. Thereafter, the substrate 100 for sample analysis may be rotated with such a number of revolutions as will apply a centrifugal force which is stronger than the capillary force in the second channel 111, whereupon the liquid in the second chamber 103 can be transferred to the third chamber 104.

Therefore, in the case where the liquid is to be transferred from the reaction chamber 107 to the second chamber 103 with the aforementioned number of revolutions, and the liquid is to be once retained in the second chamber 103 without allowing the liquid to be straightforwardly transferred to the third chamber 104, it is preferable that the second channel 111 be based on a siphon structure.

The same also applies to the first channel 110 and the third channel 112; however, a siphon structure may also be adopted even in the case where the aforementioned liquid control not needed.

In order to construct a siphon structure, given to distance R1 between the rotation axis 101 and the side face, which is closest to the rotation axis, of a chamber that is distant from the rotation axis 101, and given a distance R2 from the rotation axis 101 to a point on the first bent portion that is farthest from the rotation axis 101, it is preferable that R1>R2 (Condition 1) be satisfied.

Moreover, when a liquid which is retained in a chamber that is close to the rotation axis 101 is retained concentratedly against a side face by a centrifugal force, given a distance R4 from the rotation axis 101 to the liquid surface of the liquid, and given a distance R3 from the rotation axis 101 to a point on the second bent portion that is nearest the rotation axis 101, it is preferable that R4>R3 (Condition 2) be satisfied.

When the distances R1 to R4 are defined for the first channel 110, the second channel 111, and the third channel 112, respectively designated distances 1R1 to 1R4, 2R1 to 2R4, and 3R1 to 3R4, Conditions 1 and 2 are expressed as follows first channel 110

| | |
|---|---|
| 1R1>1R2 | Condition 1 |
| 1R4>1R3 | Condition 2 | second channel 111

| | |
|---|---|
| 2R1>2R2 | Condition 1 |
| 2R4>2R3 | Condition 2 | third channel 112

| | |
|---|---|
| 3R1>3R2 | Condition 1 |
| 3R4>3R3 | Condition 2 |

In transferring a reaction liquid by a centrifugal force from the reaction chamber 107 to the second chamber 103, the second channel 111 satisfying Conditions 1 and 2 can prevent the reaction liquid, which has been transferred to the second chamber 103, from being straightforwardly transferred to the third chamber 104. Moreover, in transferring a wash solution by a centrifugal force from the first chamber 102 to the second chamber 103, it can prevent the wash solution, which has been transferred to the second chamber 103, from being straightforwardly transferred to the third chamber 104.

Although the present embodiment has illustrated an example where the second channel 111 is a capillary channel having a siphon structure as described earlier, the first channel 110, the second channel 111, and the third channel 112 may be capillary channels lacking siphon structure, or channels utilizing gravity.

In the course of transferring a liquid from the reaction chamber 107 to the third chamber 104 via the second chamber 103, if the liquid is to be once retained in the second. chamber 103, given a second channel 111 which is a capillary channel lacking siphon structure, the following construction will be preferable. First, transfer of a liquid from the reaction chamber 107 to the second chamber 103 needs to be performed with such a number of revolutions (including also a stopped state) of the substrate 100 for sample analysis as will apply a centrifugal force which is equal to or less than a capillary force acting on the liquid filling the second channel 111. In this case, the third channel 112 is preferably a channel utilizing gravity. Moreover, in as much as the third channel 112 is a channel utilizing gravity, the side face portion 107b (shown in FIG. 3A) of the reaction chamber 107 is preferably formed so that the side face portion 107b has a dented shape for being able to retain a liquid at the side face portion 107b when the substrate 100 for sample analysis is retained at a predetermined angle. In this case, transfer of the liquid from the reaction chamber 107 to the second chamber 103 is effected by changing the rotation angle of the substrate 100 for sample analysis so that the liquid which is retained in the recess of the side face portion 107b will move through the third channel 112 based on gravity.

On the other hand, in the course of transferring a liquid from the reaction chamber 107 to the third chamber 104 via the second chamber 103, if the liquid is to be once retained in the second chamber 103, given a second channel 111 which is a channel utilizing gravity, the following construction will be preferable. The third channel 112 may be either a capillary channel (including a siphon structure) or a channel utilizing gravity; however, in the case where the third channel 112 is a channel utilizing gravity, the side face portion 103b (shown in FIG. 3A) of the second chamber 103 is preferably formed so that the side face portion 107b has a dented shape for being able to retain a liquid at the side face portion 107b when the substrate 100 for sample analysis is retained at a predetermined angle. In this case, transfer of the liquid from the second chamber 103 to the third chamber 104 is effected by changing the rotation angle of the substrate 100 for sample analysis so that the liquid which is retained in the recess of the side face portion 103b will move via the second channel 111 based on gravity.

As described above, the construction of the first channel 110, the second channel 111, and the third channel 112 may be of various types.

In the present embodiment, the first channel 110 and the third channel 112 also have a siphon structure. However, the first channel 110 and the third channel 112 may not have a siphon structure. Moreover, although the fourth channel 114 does not constitute siphon in the present embodiment, it may alternatively constitute a siphon. As will be described in detail below, in the siphon structure of the first channel 110, the second channel 111, and the third channel 112, the siphon principle governs a centrifugal force due to rotation of the substrate 100 for sample analysis.

(Operation of the Sample Analysis System 501)

Figure 5:
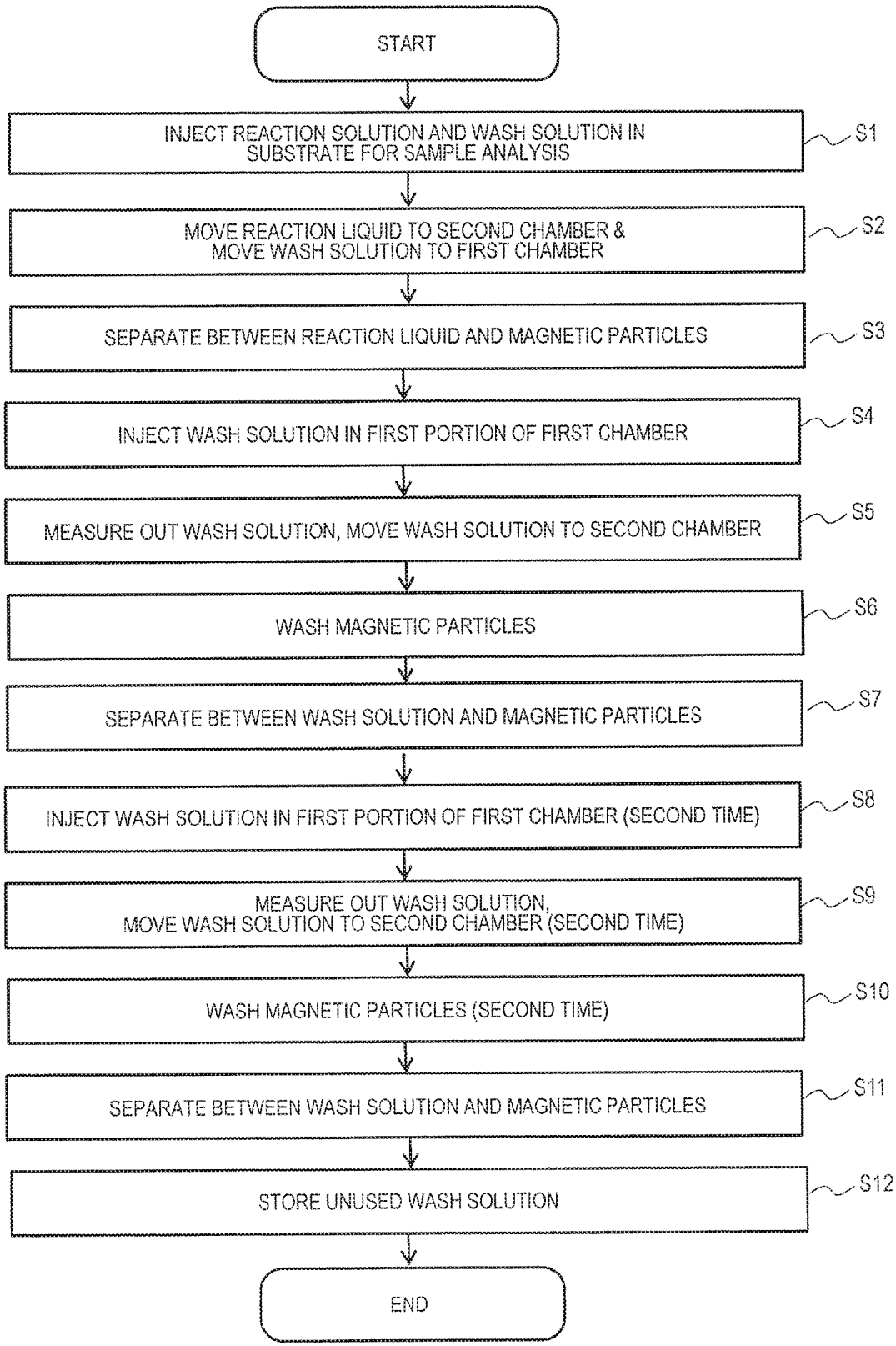
FIG. 5 A flowchart showing an exemplary operation of a sample analysis system.

An operation of the sample analysis system 501 will be described. FIG. 5 is a flowchart showing an operation of the sample analysis system 501. Prior to the following processes, the substrate 100 for sample analysis is mounted on the sample analysis device 200, and an origin of the substrate 100 for sample analysis is detected.

[Step S1]

Figure 6:
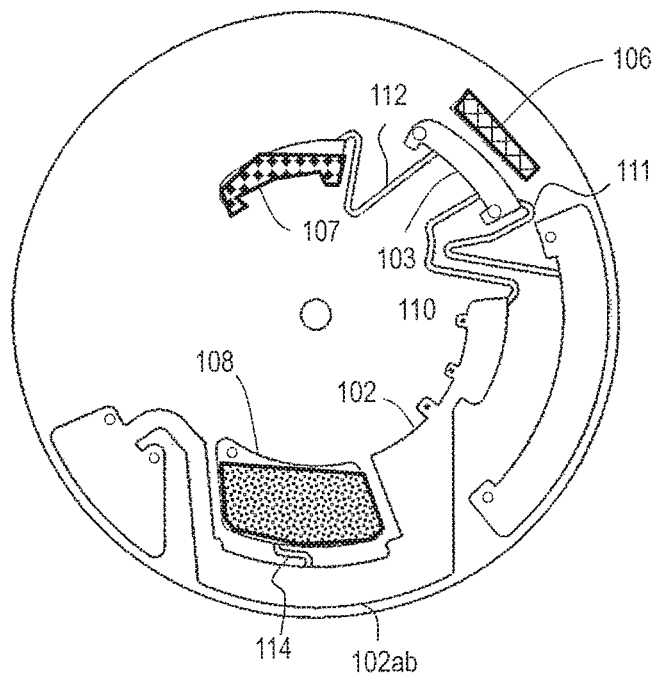
FIG. 6 A schematic diagram showing a stop angle of a substrate for sample analysis and liquid positions during operation of a sample analysis system.

First, as shown in FIG. 6, a wash solution is introduced to the first storage chamber 108 of the substrate 100 for sample analysis. Also, the magnetic-particle-immobilized antibody 305, an analyte containing the antigen 306, and the labeled antibody 308 are introduced to the reaction chamber 107.

For example, the reaction chamber 107 may retain a liquid containing the magnetic-particle-immobilized antibody 305, while chambers (not shown) that are provided in the substrate 100 for sample analysis may separately retain respective liquids containing the antigen 306 and the labeled antibody 308, and these may be transferred to the reaction chamber 107 with a centrifugal force due to rotation of the substrate 100 for sample analysis. In the reaction chamber 107, the magnetic-particle-immobilized antibody 305, the analyte containing the antigen 306, and the labeled antibody 308 are allowed to simultaneously react through antigen-antibody reactions, thus forming the composite 310. At this point, due to capillary action, the fourth channel 114 and the third channel 112 are filled with the wash solution and the reaction liquid containing the composite 310, respectively.

[Step S2]

After the composite 310 is generated, the substrate 100 for sample analysis rotated, thus moving the reaction liquid containing the composite 310 to the second chamber 103. At this point, the third channel 112 is filled with the reaction liquid due to capillary action. Therefore, as the rotation applies a centrifugal force which is stronger than the capillary force acting on the reaction liquid in the third channel 112 to the reaction involving the composite 310 in the reaction chamber 107, the reaction liquid is transferred to the second chamber 103. While the substrate 100 for sample analysis is rotating, the reaction liquid having been transferred to the second chamber 103 will not be transferred further to the third chamber 104. The reason is that, as described earlier, second channel 111 constitutes a siphon; this prevents the liquid from moving through the second channel 111 in a direction toward the rotation axis 101 against the centrifugal force.

The rotation speed of the substrate 100 for sample analysis is set to a rate such that a centrifugal force occurring through rotation ensures that the reaction liquid and other liquids will not be moved based on gravity and that a centrifugal force which is stronger than the capillary force in each capillary channel will be applied. Hereinafter, for any rotation utilizing a centrifugal force, this rotation speed will be set.

At the same time that the reaction liquid moves, the wash solution is transferred from the first storage chamber 108, through the fourth channel 114, to the bottom portion 102ab of the first chamber. Depending on the volume (size of the space) of the bottom portion 102ab and the amount of wash solution, the wash solution may fill part of the side portion 102aa.

Figure 7:
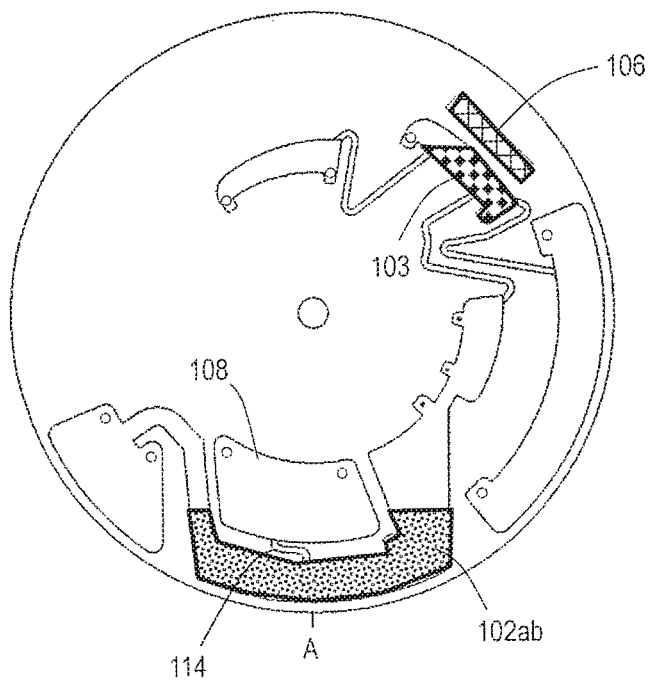
FIG. 7 A schematic diagram showing a stop angle of a substrate for sample analysis and liquid positions during operation of a sample analysis system.

After the reaction liquid and the wash solutions are entirely transferred, respectively to the second chamber 103 and the first chamber 102, the substrate 100 for sample analysis is stopped at a predetermined angle. As shown in FIG. 7, for example, the predetermined angle is an angle A at which the bottom portion 102ab of the first portion of the first chamber 102 comes below in the substrate 100 for sample analysis. Hereinafter, for ease of understanding, as shown in FIG. 7, in a substrate 100 for sample analysis which is retained so that the rotation axis 101 is inclined at an angle θ from the direction of gravity, any angle of the substrate 100 for sample analysis will be represented relative to the vertical direction of the rotation axis 101. At this point, the second channel 111 is filled with the reaction liquid due to capillary action. The angle A is to be selected from within an angle range in which the wash solution that is in the second portion 102a of the first chamber 102 will not move to the first portion 102b based on gravity.

[Step S3]

The substrate 100 for sample analysis is rotated. A centrifugal force occurs with the rotation, which acts on the reaction liquid and the magnetic particles 311 in the second chamber 103. This centrifugal force acts so that the liquid and the composite will move toward the side face 103b of the second chamber 103, as shown in FIG. 3A. The direction in which the centrifugal force acts is identical to the direction of the attractive force that the magnetic particles 311 receive from the magnet 106. Therefore, the composite 310 is strongly pressed against the side face 103b.

Under the centrifugal force, the reaction liquid is discharged from the second channel 111, and transferred to the third chamber 104. With a sum of the centrifugal force and the attractive force of the magnet 106, the magnetic particles 311 are strongly pressed against the side face 103b, and captured. As a result, only the reaction liquid is discharged from the second channel 111, while the magnetic particles 311 remain in the second chamber 103.

At this time, the wash solution which has been at the bottom portion 102ab of the first portion 102b of the first chamber 102 is pressed by the centrifugal force against the side face of the bottom portion 102ab that is away from the rotation axis 101, so that the wash solution is essentially remaining in the first portion 102b.

Figure 8:
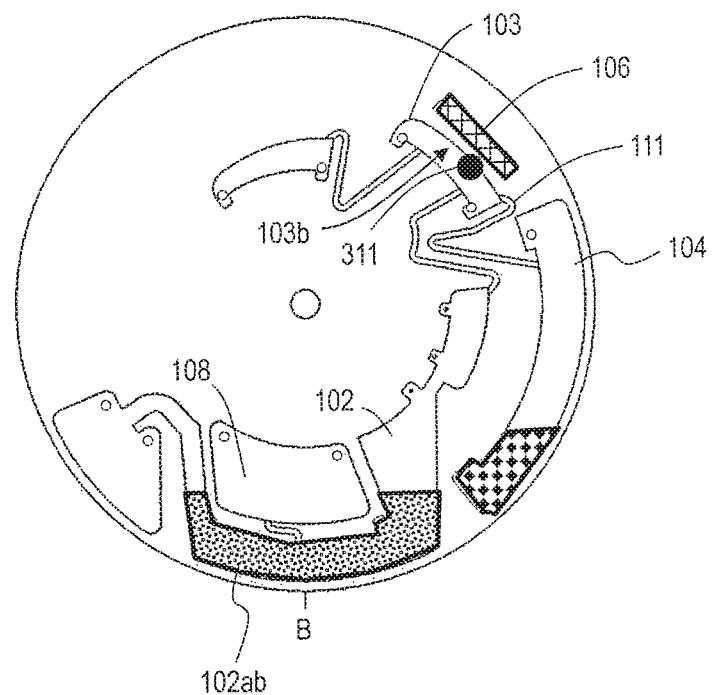
FIG. 8 A schematic diagram showing a stop angle of a substrate for sample analysis and liquid positions during operation of a sample analysis system.

As shown in FIG. 8, after the liquid has all moved to the third chamber 104, for example, rotation of the substrate 100 for sample analysis is stopped at an angle B. As a result, the reaction liquid and the magnetic particles 311 become separated. Specifically, the reaction liquid moves to the third chamber 104 while the magnetic particles 311 remain, in the second chamber 103. As shown in FIG. 8, even after rotation of the substrate 100 for sample analysis is stopped, due to the attractive force received from the magnet 106, the magnetic particles 311 are able to remain gathered at the side face 103b. The angle B may be equal to the angle A, or coincide with the angle C in the next step. In this case, upon stopping of the substrate rotation, the wash solution which is at the second portion 102a of the first chamber 102 moves to the first portion 102b based on gravity.

[Step S4 (Process (a))]

Figure 9:
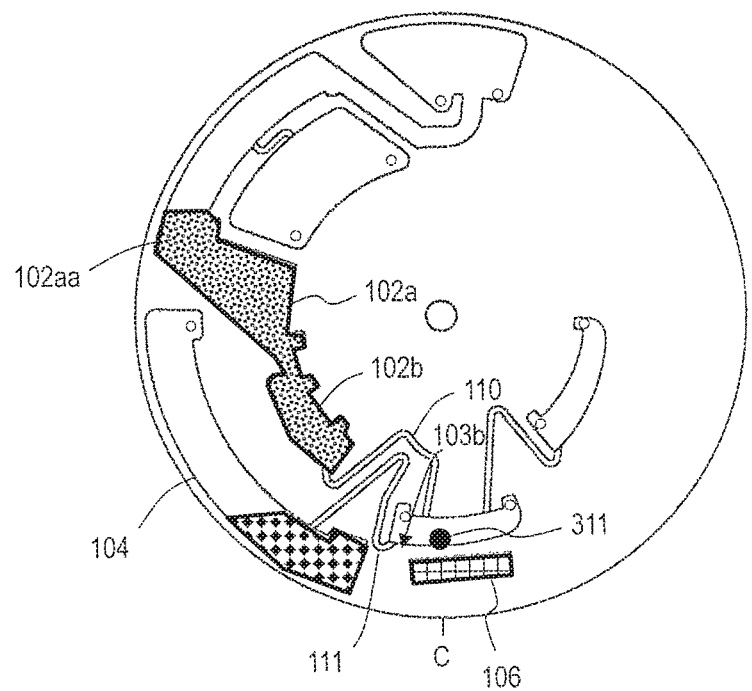
FIG. 9 A schematic diagram showing a stop angle of substrate for sample analysis and liquid positions during operation of a sample analysis system.

As shown in FIG. 9, the substrate 100 for sample analysis is slightly rotated, and stopped at an angle C (first angle). As a result, the first portion 102b of the first chamber 102 is situated below the second portion 102a along the gravity direction, and a portion of the wash solution in the second portion 102a moves within the first chamber 102 based on gravity, thus filling at least a part of the first portion 102b. In order to surely fill the first portion 102b with the wash solution, clockwise and counterclockwise rotations may be alternated to about several degrees around the angle C, i.e., swung. Thus, as shown in FIG. 9, for example, the first portion 102b and the side portion 102aa of the second portion 102a are filled with the wash solution. Once the first portion 102b becomes filled with the wash solution, the first channel 110 draws in the wash solution via capillary action. In other words, the first channel 110 is filled with the wash solution due to capillary action. The angle C may be any angle that allows the wash solution to move from the second portion 102a to the first portion 102b based on gravity.

[Step S5 (Process (b))]

Figure 10A:
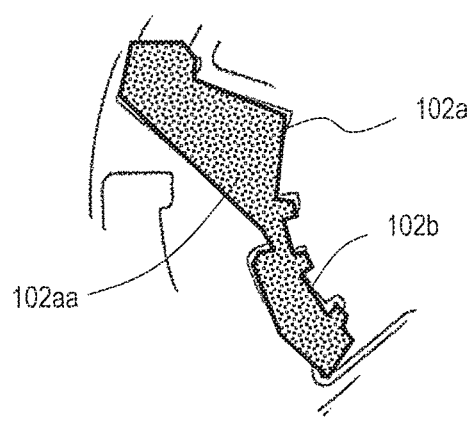
FIG. 10A A diagram explaining an example of measuring out a liquid in a first chamber.
Figure 10B:
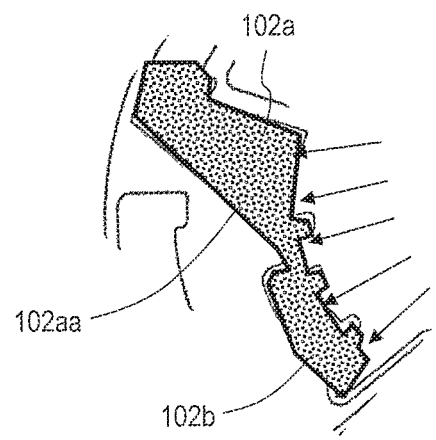
FIG. 10B An exemplary diagram explaining measuring out a liquid in the first chamber.
Figure 10C:
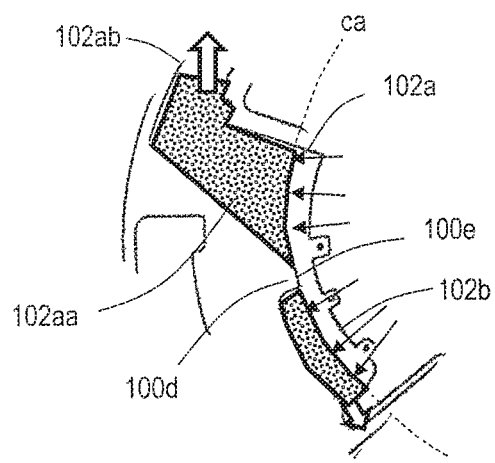
FIG. 10C An exemplary diagram explaining measuring out a liquid in the first chamber.
Figure 10D:
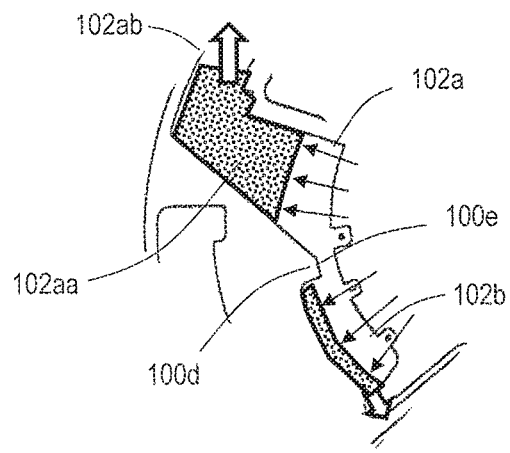
FIG. 10D An exemplary diagram explaining measuring out a liquid in the first chamber.

Next, the substrate 100 for sample analysis is rotated. As shown in FIG. 10A and FIG. 10B, a centrifugal force due to rotation acts on the wash solution which is in the first portion 102b and the side portion 102aa of the second portion 102a. The centrifugal force acts on the wash solution in a direction away from the rotation axis 101. Therefore, as shown in FIG. 10C, the wash solution which exists in the first portion 102b moves through the coupling portion 102c to the side portion 102aa of the second portion 102a. The wash solution which is in the side portion 102aa of the second portion 102a moves to the bottom portion 102ab, which is more distant from the rotation axis. Consequently, a superfluous amount out of the wash solution retained in the first portion 102b is returned to the second portion 102a, so that the circular arc ca whose radius is a line segment connecting the rotation axis 101 and the point 100e on the wall portion 100f that is the closest to the rotation axis 101 will align with the liquid surface of the wash solution in the first portion 102b. As a result of this, a predetermined amount of wash solution is measured out in the first portion 102b. With a centrifugal force due to rotation, the wash solution which has been measured out is transferred via the first channel 110 to the second chamber 103, as shown in FIG. 10D.

[Step S6 (Process (e))]

Figure 11:
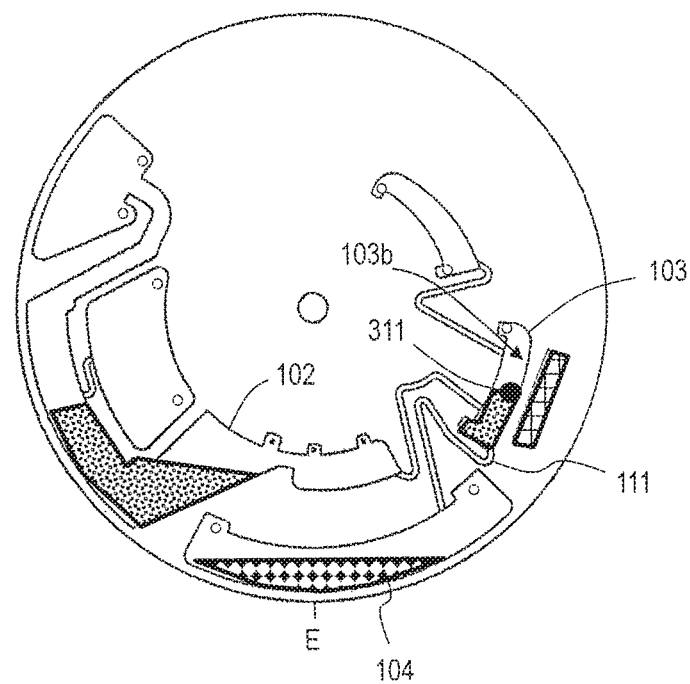
FIG. 11 A schematic diagram showing a stop angle of a substrate for sample analysis and liquid positions during operation of a sample analysis system.

Once the wash solution has moved to the second chamber 103, for example, rotation of the substrate 100 for sample analysis is stopped at the angle D (third angle), as shown in FIG. 11. As a result, the magnetic particles 311 which were captured by the second chamber 103 are washed by the wash solution. Moreover, a portion of the wash solution in the second chamber 103 moves to the second channel 111 via capillary action.

[Step S7 (Process (f))]

Figure 12:
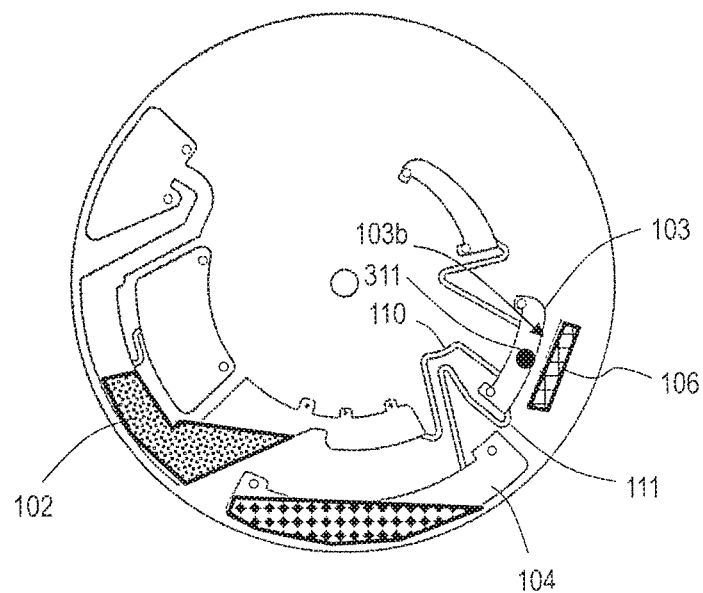
FIG. 12 A schematic diagram showing a stop angle of a substrate for sample analysis and liquid positions during operation of a sample analysis system.

The substrate 100 for sample analysis is rotated. A centrifugal force occurs with rotation, whereby the wash solution in the second chamber 103 is transferred through the second channel 111 to the third chamber 104. With a sum of the centrifugal force and the attractive force of the magnet 106, the magnetic particles 311 are strongly pressed against the side face 103b and captured. Therefore, as shown in FIG. 12, only the wash solution is discharged from the second chamber 111, while the magnetic particles 311 remain in the second chamber 103.

On the other hand, due to centrifugal force, the wash solution in the first chamber 102 is kept substantially retained in the second portion 102a. Therefore, there occurs essentially no transfer of the wash solution in the first chamber 102 to the second chamber 103.

[Step S8 (Process (c))]

Figure 13:
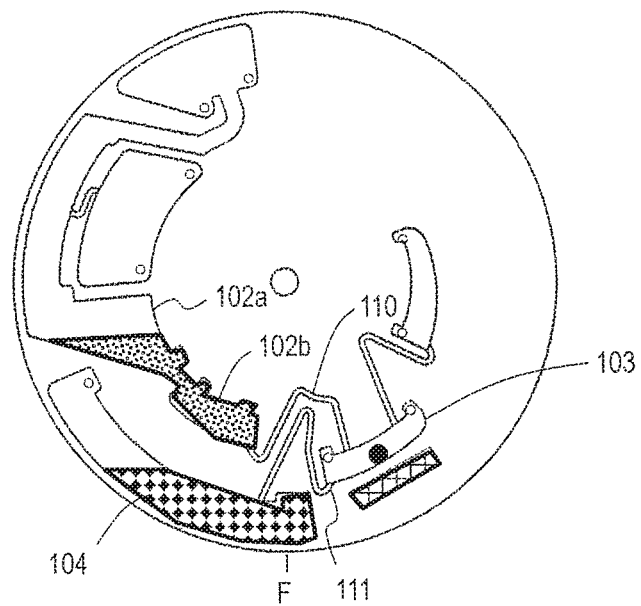
FIG. 13 An exemplary schematic diagram showing a stop angle of a substrate for sample analysis and liquid positions during operation of a sample analysis system.

Essentially the same as step S4. As shown in FIG. 13, the substrate 100 for sample analysis is stopped at an angle E (second angle). As a result, the first portion 102b of the first chamber 102 is situated below the second portion 102a along the gravity direction, and a portion of the wash solution in the second portion 102a moves within the first chamber 102 based on gravity, thus filling at least a part of the first portion 102b. In order to surely fill the first portion 102b with the wash solution, clockwise and counterclockwise rotations may be made to about several degrees around the angle E, i.e., swung. Consequently, for example, the first portion 102b and a part of the side portion 102aa of the second portion 102a are filled with the wash solution. Once the first portion 102b becomes filled with the wash solution, the first channel 110 draws in the wash solution via capillary action. In other words, the first channel 110 is filled with the wash solution due to capillary action. The angle E may be any angle that allows the wash solution to move from the second portion 102a to the first portion 102b based on gravity. The angle E may be identical to the angle C. Since there is less wash solution retained in the first chamber 102 than at step S4, it may be stopped at a larger angle than the angle C, relative to the angle A.

[Step S9 (Process (d))]

Next, the substrate 100 for sample analysis is rotated. As has been explained at step S5, a centrifugal force due to rotation acts on the wash solution which is in the first portion 102b and the side portion 102aa of the second portion 102a. Therefore, the wash solution which exists in the first portion 102b moves through the coupling portion 102c to the side portion 102aa of the second portion 102a. The wash solution which is in the side portion 102aa of the second portion 102a moves to the bottom portion 102ab, which is more distant from the rotation axis. Consequently, a superfluous amount out of the wash solution retained in the first portion 102b is returned to the second portion 102a. As a result, a predetermined amount of wash solution is measured out in the first portion 102b. Moreover, a superfluous amount out of the wash solution retained in the first portion 102b is returned to the second portion 102a. With a centrifugal force due to rotation, the wash solution which has been measured out is transferred via the first channel 110 to the second chamber 103, ash FIG. 10D. Also, substantially the predetermined amount of wash solution which has been measured out is transferred via the first channel 110 to the second chamber 103.

[Step S10 (Process (g))]

Figure 14:
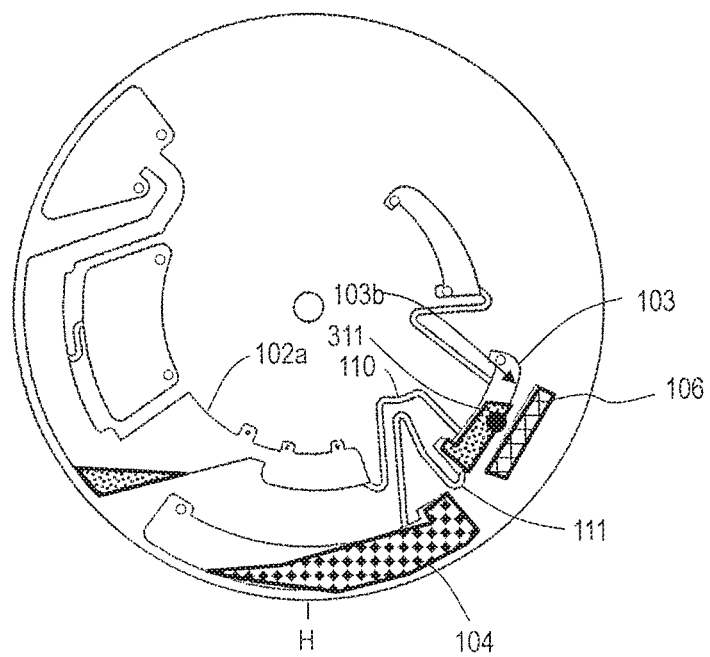
FIG. 14 A schematic diagram showing an example of a stop angle of a substrate for sample analysis and liquid positions during operation of a sample analysis system.

Once the wash solution has moved to the second chamber 103, for example, rotation of the substrate 100 for sample analysis is stopped at an angle F (fourth angle), as shown in FIG. 14. As a result, the magnetic particles 311 which were captured by the second chamber 103 are again washed the wash solution. Moreover, a portion of the wash solution in the second chamber 103 moves to the second channel 111 via capillary action.

[Step S11 (Process (h))]

Figure 15:
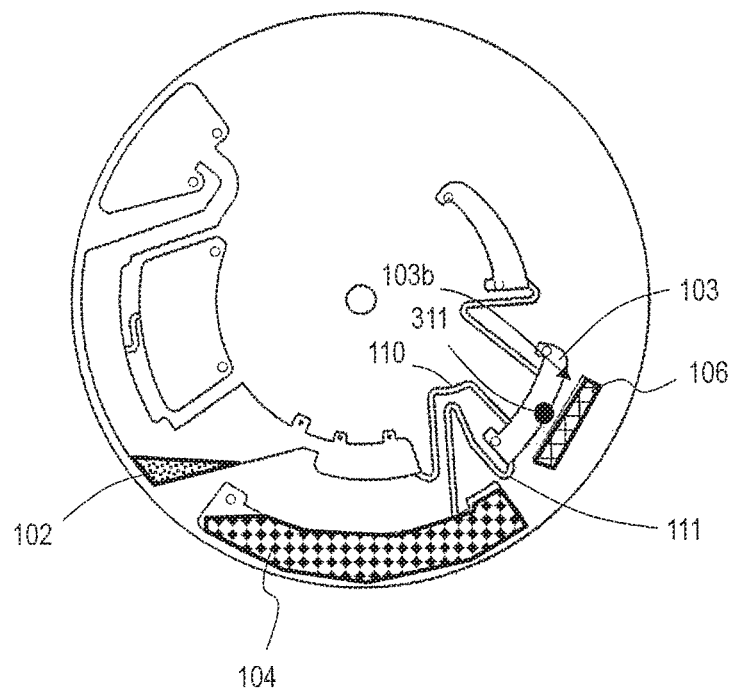
FIG. 15 A schematic diagram showing an example of a stop angle of a substrate for sample analysis and liquid positions during operation of a sample analysis system.

The substrate 100 for sample analysis rotated. A centrifugal force occurs with rotation, whereby the wash solution in the second chamber 103 is transferred through the second channel 111 to the third chamber 104. With a sum of the centrifugal force and the attractive force of the magnet 106, the magnetic particles 311 are strongly pressed against the side face 103b and captured. Therefore, as shown in FIG. 15, only the wash solution is discharged from the second channel 111, while the magnetic particles 311 remain in the second chamber 103.

At this time, the wash solution which has been at the bottom portion 102ab of the first portion 102b of the first chamber 102 is pressed by the centrifugal force against the side face of the bottom portion 102ab that is away from the rotation axis 101, so that the wash solution is essentially remaining in the first portion 102b.

[Step S12]

Figure 16:
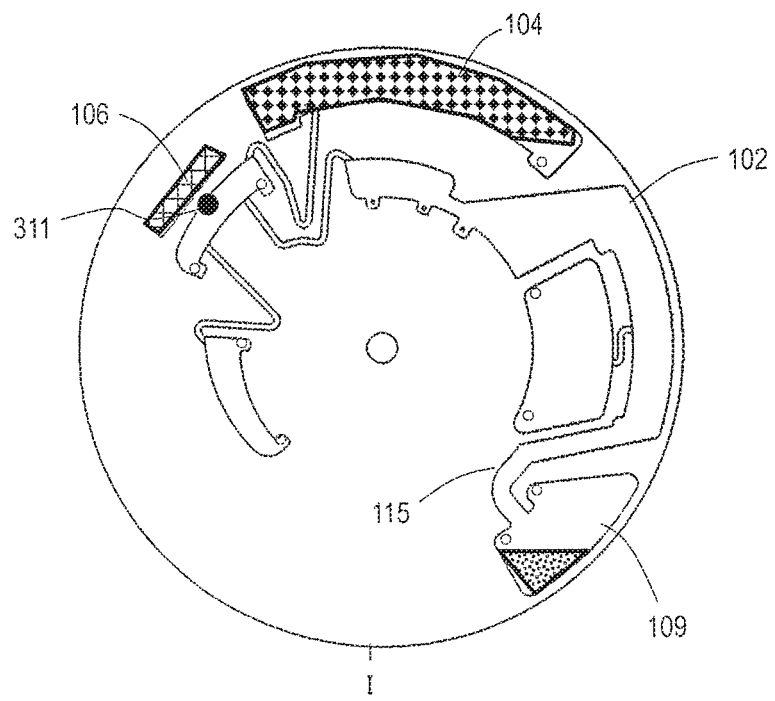
FIG. 16 A schematic diagram showing an example of a stop angle of a substrate for sample analysis and liquid positions during operation of a sample analysis system.

As shown in FIG. 16, after the wash solution has all moved to the third chamber 104, for example, rotation of the substrate 100 for sample analysis is stopped at an angle G. As the angle G, an angle is selected such that the wash solution remaining in the first chamber 102 is able to move through the fifth channel 115 to the second storage chamber 109 based on gravity.

Through the above processes, B/F separation, or specifically, a separation between the magnetic particles 311 and various unreacted substances occurs.

Thereafter, the optical measurement unit 207 is used to detect dye, luminescence, fluorescence, or other signals which are in accordance with the label substance 307 of the labeled antibody 308 having been bound to the composite 310 contained in the magnetic particles 311. Thus, it is possible to achieve detection of the antigen 306, quantification of the concentration of the antigen 306, and so on.

Thus, with a substrate for sample analysis, a sample analysis device, and a sample analysis system according to the present embodiment, a liquid can be introduced into the same chamber separately in multiple instances. Therefore, sufficient washing can be attained when the substrate for sample analysis is used in effecting B/F separation. Moreover, this operation can be realized through control of the rotation and stopping of the substrate for sample analysis, and control of the stopping angles. Hence, without involving the use of a large-sized analysis apparatus or manual maneuvering by an operator, they are suitably applicable to assay techniques that carry out analysis of components within an analyte through complicated reaction steps, including B/F separation.

The above embodiment illustrates an example of washing in B/F separation. However, a substrate for sample analysis, and a sample analysis device according to the present embodiment are applicable to various methods of sample analysis for introducing solutions that are not wash solutions to the same chamber over multiple times as described above. Although introduction of liquids to chambers is performed in consecutive manners in the above embodiment, appropriate control of rotation and stop of the substrate for sample analysis and appropriate control of the stopping angle would make it possible to include other processes in between, Although washing is performed twice in the above embodiment, it may be performed three or more as necessary.

Although the above embodiment has described an example of performing a sample analysis by using magnetic particles, the substrate for sample analysis, sample analysis device, sample analysis system, and program for a sample analysis system according to the present disclosure are not limited to a sample analysis by using magnetic particles. For example, rather than magnetic particles, it may be a wall surface within the chamber that the primary antibody is immobilized to.

Specifically, in the case where the chamber is composed of a material such as polystyrene or polycarbonate, the primary antibody can be immobilized to a wall surface within the chamber through physisorption. Thus, a sandwiched type of combination reaction with the antigen or the labeled antibody can be effected within the chamber. Moreover, a functional group capable of binding to the primary antibody (e.g., an amino group or a carboxyl group) may be present on the wall surfaces in the chamber, to which a primary antibody may be immobilized via a chemical bond. As a result, a sandwiched type of combination reaction with the antigen or the labeled antibody can be effected within the chamber. Moreover, a metal substrate may be provided on the wall surface within the chamber, and the primary antibody may be allowed to bind to the metal substrate by using a SAM, thereby immobilizing the primary antibody. As a result, a sandwiched type of combination reaction with the antigen or the labeled antibody can be effected within the chamber.

The implementation which immobilizes the primary antibody to the wall surface in the chamber through physisorption or via a chemical bond can be used in a measurement system which detects a dye, chemiluminescence, or fluorescence signal, for example. On the other hand, the implementation which immobilizes the primary antibody to a metal substrate can be used in a measurement system which detects mainly an electrochemical signal (e.g., an electric current) or an electrochemiluminescence signal as the signal.

Figure 3C:
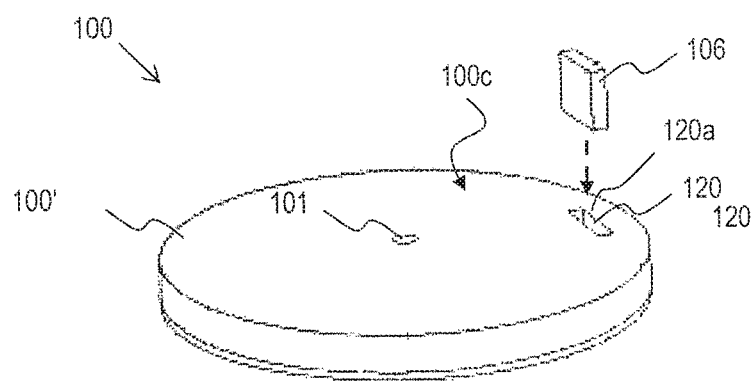
FIG. 3C A perspective view showing another exemplary structure of a substrate for sample analysis.

In these cases, the magnet 106 shown in FIG. 3 is unnecessary. Moreover, the reaction field in which to form the composite 310 is not the reaction chamber 107 but the third chamber 104. Therefore, the primary antibody is immobilized to the wall surface of the third chamber 104. Moreover, the substrate for sample analysis, sample analysis device, sample analysis system, and program for a sample analysis system according to the present disclosure are applicable to not only non-competitive assays(sandwich immunoassay) but also competitive assays and genetic detection techniques based on hybridization.

INDUSTRIAL APPLICABILITY

The substrate for sample analysis, sample analysis device, sample analysis system, and program for a sample analysis system disclosed herein are applicable to the analysis of a specific component within an analyte by utilizing various reactions.

REFERENCE SIGNS LIST

100 substrate for sample analysis
100' substrate
100a base substrate
100b cover substrate
100d wall portion
101 rotation axis
102 first chamber
102a second portion
102aa side portion
102ab bottom portion
102b first portion
102c coupling portion
103 second chamber
103b side face
104 third chamber
106 magnet
107 reaction chamber
108 first storage chamber
109 second storage chamber
110 first channel
111 second channel
112 third channel
114 fourth channel
115 fifth channel
118 air hole
119 opening
200 sample analysis device
201 motor
201a turntable
203 origin detector
204 rotation angle detection circuit
205 control circuit
206 drive circuit
207 optical measurement unit
302 magnetic particles
304 primary antibody
305 magnetic-particle-immobilized antibody
306 antigen
307 label substance
308 labeled antibody
310 composite
501 sample analysis system

The invention claimed is:

1. A substrate for sample analysis on which transfer of a liquid is to occur with rotational motion, the substrate for sample analysis comprising:
a substrate having a rotation axis;
a first chamber being located in the substrate and having a first space for retaining a liquid;
a second chamber being located in the substrate and having a second space for retaining the liquid to be discharged from the first chamber; and
a first channel being located in the substrate and having a path connecting the first chamber and the second chamber, the first channel being capable of being filled via capillary action with the liquid retained in the first space, wherein,
the first space of the first chamber includes a first portion and a second portion, and a coupling portion being located between the first portion and the second portion and coupling the first portion and the second portion;
the substrate has a wall portion partitioning the first portion and the second portion of the first space from each other;
the second chamber is more distant from the rotation axis than is the first portion of the first chamber;
the coupling portion of the first space is closer to the rotation axis than is the wall portion of the substrate;
a portion of the first portion of the first space that is, as viewed from a direction which is parallel to the rotation axis, located outward of a circle which is centered around the rotation axis and whose radius is segment connecting the rotation axis and a point on the wall portion that is the closest to the rotation axis is ½ or less in volumetric capacity to that of the first space; and
the first channel is connected to the first portion of the first space.

2. The substrate for sample analysis of claim 1, wherein a distance from the rotation axis to a position on the first portion at which the first channel is connected is longer than a distance from the rotation axis to a point on the wall portion that is the closest to the rotation axis.

3. The substrate for sample analysis of claim 1, wherein the first portion of the first space includes a portion located outward of a circular arc which is centered around the rotation axis and whose radius is a line segment connecting the rotation axis and a point on the wall portion that is the closest to the rotation axis.

4. The substrate for sample analysis of claim 1, wherein the second portion of the first space includes a portion located outward of a circular arc which is centered around the rotation axis and whose radius is a line segment connecting the rotation axis and a point on the wall portion that is the closest to the rotation axis.

5. The substrate for sample analysis of claim 3, wherein the second portion of the first space includes a portion which is more distant from the rotation axis than is the first portion.

6. The substrate for sample analysis of claim 1, wherein the second space is greater in volumetric capacity than a portion of the first portion of the first space that is, as viewed from a direction which is parallel to the rotation axis, located outward of a circle which is centered around the rotation axis and whose radius is a line segment connecting the rotation axis and a point on the wall portion that is the closest to the rotation axis.

7. The substrate for sample analysis of claim 1, further comprising:
a third chamber being in the substrate located more distant from the rotation axis than is the second chamber and having a third space for retaining of the liquid to be discharged from the second chamber; and
a second channel being located in the substrate and having a path connecting the second chamber and the third chamber, the second channel capable of being filled via capillary action with the liquid that is retained in the second space.

8. The substrate for sample analysis of claim 7, wherein,
the second channel includes a first bent portion which is convex toward an opposite side from the rotation axis and a second bent portion which is convex toward the rotation axis, the first bent portion being located between the second bent portion and the second chamber;
a distance from the rotation axis to the third chamber is longer than a distance from the rotation axis to an apex of the first bent portion; and
a distance from the rotation axis to a liquid surface of the liquid that is retained in the third chamber as created by a centrifugal force due to rotation of the substrate is longer than a distance from the rotation axis to an apex of the second bent portion.

9. The substrate for sample analysis of claim 8, wherein,
the first channel includes a first bent portion which is convex toward an opposite side from the rotation axis and a second bent portion which is convex toward the rotation axis, the first bent portion being located between the second bent portion and the first chamber;
a distance from the rotation axis to the second chamber is longer than a distance from the rotation axis to an apex of the first bent portion; and
a distance from the rotation axis to a liquid surface of the liquid that is retained in the first chamber as created by a centrifugal force due to rotation of the substrate is longer than a distance from the rotation axis to an apex of the second bent portion.

10. The substrate for sample analysis of claim 1, further comprising a magnet located near the second chamber.

11. A sample analysis system comprising:
the substrate for sample analysis of claim 10; and
a sample analysis device, including
a motor to rotate the substrate for sample analysis around the rotation axis in a state where the rotation axis is inclined at an angle which is greater than 0° but not more than 90° with respect to the direction of gravity,
a rotation angle detection circuit to detect an angle of a shaft of the motor,
a drive circuit to control rotation and a stopping angle of the motor based on a result of detection by the rotation angle detection circuit, and
a control circuit including an arithmetic unit, a memory, and a program which is stored in the memory and executable by the arithmetic unit, to control based on the program an operation of the motor, the rotation angle detection circuit, the origin detector, and the drive circuit,
wherein,
when the substrate for sample analysis with the first chamber being filled with the liquid is placed on a turntable of the sample analysis device,
the program comprises the processes of:
(a) stopping the substrate for sample analysis at a predetermined first angle to allow a portion of the liquid to move within the first chamber based on gravity, fill at least a part of the first portion of the first chamber with the portion of the liquid, and transfer another portion of the liquid to the first channel via capillary action,
(b) rotating the sample analysis substrate at a rate causing a centrifugal force which is stronger than a capillary force acting on the liquid filling the first channel to, with a centrifugal force due to rotation of the substrate, measure out a portion of the liquid in the first portion, move excess liquid to the second portion to thereby allow the remaining liquid to be retained in the second portion, and move the measured portion of the liquid in the first portion to the second chamber through the first channel,
(c) stopping the substrate for sample analysis at a predetermined second angle to allow a portion of the remaining liquid to move within the first chamber based on gravity, fill at least a part of the first portion of the first chamber with the portion of the remaining liquid, and transfer another portion of the remaining liquid to the first channel via capillary action, and
(d) rotating the sample analysis substrate at a rate causing a centrifugal force which is stronger than a capillary force acting on the liquid filling the first channel to, with a centrifugal force due to rotation of the substrate, measure out a portion of the remaining liquid in the first portion, move excess liquid to the second portion to thereby allow the superfluous liquid to be retained in the second portion, and move the measured portion of the remaining liquid in the first portion to the second chamber through the first channel.

12. The sample analysis system of claim 11, further comprising, between the process (b) and the process (c), the processes of:
(e) stopping the substrate for sample analysis at a predetermined third angle to transfer a portion of the liquid in the second chamber to the second channel via capillary action; and
(f) rotating the sample analysis substrate at a rate causing a centrifugal force which is stronger than a capillary force acting on the liquid filling the second channel to, with a centrifugal force due to rotation of the substrate, move the liquid in the second chamber to the third chamber through the second channel.

13. The sample analysis system of claim 12, further comprising, after the process (d), the processes of:
(g) stopping the substrate for sample analysis at a predetermined fourth angle to transfer a portion of the liquid in the second chamber to the second channel via capillary action; and
(h) rotating the sample analysis substrate at a rate causing a centrifugal force which is stronger than a capillary force acting on the liquid filling the second channel to, with a centrifugal force due to rotation of the substrate, move the liquid in the second chamber to the third chamber through the second channel.

14. The sample analysis system of claim 11, wherein, in at least one of the processes (a) and (b), after stopping rotation of the substrate for sample analysis, the substrate is allowed to alternately rotate clockwise or counterclockwise by a predetermined angle.

15. A sample analysis device comprising:
a motor to rotate the substrate for sample analysis of claim 10 around the rotation axis in a state where the rotation axis is inclined at an angle which is greater than 0° but not more than 90° with respect to the direction of gravity,
a rotation angle detection circuit to detect an angle of a shaft of the motor, a drive circuit to control rotation and a stopping angle of the motor based on a result of detection by the rotation angle detection circuit, and a control circuit including an arithmetic unit, a memory, and a program which is stored in the memory and executable by the arithmetic unit, to control based on the program an operation of the motor, the rotation angle detection circuit, and the drive circuit, wherein, when the substrate for sample analysis with the first chamber being filled with the liquid is placed on a turntable of the sample analysis device, the program comprises the processes of:

(a) stopping the substrate for sample analysis at a predetermined first angle to allow a portion of the liquid to move within the first chamber based on gravity, fill at least a part of the first portion of the first chamber with the portion of the liquid, and transfer another portion of the liquid to the first channel via capillary action, (b) rotating the sample analysis substrate at a rate causing a centrifugal force which is stronger than a capillary force acting on the liquid filling the first channel to, with a centrifugal force due to rotation of the substrate, measure out a portion of the liquid in the first portion, move excess liquid to the second portion to thereby allow the remaining liquid to be retained in the second portion, and move the measured portion of the liquid in the first portion to the second chamber through the first channel, (c) stopping the substrate for sample analysis at a predetermined second angle to allow a portion of the remaining liquid to move within the first chamber based on gravity, fill at least a part of the first portion of the first chamber with the portion of the remaining liquid, and transfer another portion of the remaining liquid to the first channel via capillary action, and (d) rotating the sample analysis substrate at a rate causing a centrifugal force which is stronger than a capillary force acting on the liquid filling the first channel to, with a centrifugal force due to rotation of the substrate, measure out a portion of the remaining liquid in the first portion, move excess liquid to the second portion to thereby allow the superfluous liquid to be retained in the second portion, and move the measured portion of the remaining liquid in the first portion to the second chamber through the first channel.

16. A non-transitory computer-readable storage medium storing a program for a sample analysis system comprising:
the substrate for sample analysis of claim 7; and
a sample analysis device, including
a motor to rotate the substrate for sample analysis around the rotation axis in a state where the rotation axis is inclined at an angle which is greater than 0° but not more than 90° with respect to the direction of gravity, a rotation angle detection circuit to detect an angle of a shaft of the motor, a drive circuit to control rotation and a stopping angle of the motor based on a result of detection by the rotation angle detection circuit, and a control circuit including an arithmetic unit, a memory, and a program which is stored in the memory and executable by the arithmetic unit, to control based on the program an operation of the motor, the rotation angle detection circuit, the origin detector, and the drive circuit, wherein, when the substrate for sample analysis with the first chamber being filled with the liquid is placed on a turntable of the sample analysis device, the program comprises the processes of:

(a) stopping the substrate for sample analysis at a predetermined first angle to allow a portion of the liquid to move within the first chamber based on gravity, fill at least a part of the first portion of the first chamber with the portion of the liquid, and transfer another portion of the liquid to the first channel via capillary action, (b) rotating the sample analysis substrate at a rate causing a centrifugal force which is stronger than a capillary force acting on the liquid filling the first channel to, with a centrifugal force due to rotation of the substrate, measure out a portion of the liquid in the first portion, move excess liquid to the second portion to thereby allow the remaining liquid to be retained in the second portion, and move the measured portion of the liquid in the first portion to the second chamber through the first channel, (c) stopping the substrate for sample analysis at a predetermined second angle to allow a portion of the remaining liquid to move within the first chamber based on gravity, fill at least a part of the first portion of the first chamber with the portion of the remaining liquid, and transfer another portion of the remaining liquid to the first channel via capillary action, and (d) rotating the sample analysis substrate at a rate causing a centrifugal force which is stronger than a capillary force acting on the liquid filling the first channel to, with a centrifugal force due to rotation of the substrate, measure out a portion of the remaining liquid in the first portion, move excess liquid to the second portion to thereby allow the superfluous liquid to be retained in the second portion, and move the measured portion of the remaining liquid in the first portion to the second chamber through the first channel.

* * * * *